United States Patent
Vicente et al.

(10) Patent No.: US 8,844,007 B2
(45) Date of Patent: Sep. 23, 2014

(54) SYSTEMS AND METHODS FOR PROCESSING AND TRANSMITTING SENSOR DATA

(75) Inventors: Kenneth San Vicente, San Diego, CA (US); Indrawati Gauba, San Diego, CA (US); Siddharth Waichal, Pune (IN); Andrew Walker, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 105 days.

(21) Appl. No.: 13/441,621

(22) Filed: Apr. 6, 2012

(65) Prior Publication Data
US 2012/0260323 A1 Oct. 11, 2012

Related U.S. Application Data

(60) Provisional application No. 61/473,661, filed on Apr. 8, 2011.

(51) Int. Cl.
*H04L 9/32* (2006.01)
*H04L 29/06* (2006.01)
*H04B 1/02* (2006.01)
*G06F 7/04* (2006.01)
*G06F 12/00* (2006.01)
*A61B 5/00* (2006.01)
*A61B 5/145* (2006.01)
*A61B 5/1495* (2006.01)
*G06F 19/00* (2011.01)

(52) U.S. Cl.
CPC ............ *A61B 5/002* (2013.01); *A61B 5/14532* (2013.01); *A61B 2562/08* (2013.01); *A61B 5/1495* (2013.01); *G06F 19/3418* (2013.01)
USPC .............. 726/6; 455/41.3; 600/365; 713/168; 726/19; 726/27

(58) Field of Classification Search
None
See application file for complete search history.

(56) References Cited

U.S. PATENT DOCUMENTS 6,564,105 B2 5/2003 Starkweather et al.
6,571,128 B2 5/2003 Lebel et al.
(Continued)

FOREIGN PATENT DOCUMENTS

EP 1445893 A2 * 8/2004
EP 2172863 A2 4/2010
(Continued)

OTHER PUBLICATIONS

Dynastream Innovations, Inc.: ANT Message Protocol and Usage (Jul. 2, 1 2007).
(Continued)

*Primary Examiner* — Fatoumata Traore
(74) *Attorney, Agent, or Firm* — Knobbe Martens Olson & Bear, LLP.

(57) ABSTRACT

Systems and methods for continuous measurement of an analyte in a host are provided. The system generally includes a continuous analyte sensor configured to continuously measure a concentration of analyte in a host and a sensor electronics module physically connected to the continuous analyte sensor during sensor use, wherein the sensor electronics module is further configured to directly wirelessly communicate sensor information to one or more display devices. Establishment of communication between devices can involve using a unique identifier associated with the sensor electronics module to authenticate communication. Times tracked at the sensor electronics module and the display module can be at different resolutions, and the different resolutions can be translated to facilitate communication. In addition, the frequency of establishing communication channels between the sensor electronics module and the display devices can vary depending upon whether reference calibration information is being updated.

15 Claims, 8 Drawing Sheets

(56) References Cited

U.S. PATENT DOCUMENTS

| | | |
|---|---|---|
| 6,585,644 B2 | 7/2003 | Lebel et al. |
| 6,659,948 B2 | 12/2003 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,958,705 B2 | 10/2005 | Lebel et al. |
| 7,098,803 B2 | 8/2006 | Mann et al. |
| 7,369,635 B2 | 5/2008 | Spital et al. |
| 7,587,287 B2 | 9/2009 | Connolly et al. |
| 7,722,536 B2 | 5/2010 | Goodnow |
| 7,768,408 B2 | 8/2010 | Reggiardo et al. |
| 7,801,582 B2 | 9/2010 | Peyser |
| 7,811,231 B2 | 10/2010 | Jin et al. |
| 7,826,382 B2 | 11/2010 | Sicurello et al. |
| 7,884,729 B2 | 2/2011 | Reggiardo et al. |
| 7,948,370 B2 | 5/2011 | Reggiardo et al. |
| 7,949,404 B2 | 5/2011 | Hill |
| 8,029,443 B2 | 10/2011 | Goodnow |
| 8,066,639 B2 | 11/2011 | Nelson et al. |
| 8,085,151 B2 | 12/2011 | Jennewine |
| 8,086,292 B2 | 12/2011 | Peyser |
| 8,089,363 B2 | 1/2012 | Reggiardo et al. |
| 8,123,686 B2 | 2/2012 | Fennell et al. |
| 8,187,183 B2 | 5/2012 | Jin et al. |
| 8,372,351 B2 | 2/2013 | Ow-Wing |
| 8,437,966 B2 | 5/2013 | Connolly et al. |
| 2005/0182306 A1* | 8/2005 | Sloan ............................ 600/300 |
| 2006/0166629 A1 | 7/2006 | Reggiardo |
| 2008/0060955 A1 | 3/2008 | Goodnow |
| 2008/0319296 A1 | 12/2008 | Bernstein et al. |
| 2008/0320587 A1* | 12/2008 | Vauclair et al. ................. 726/17 |
| 2009/0036760 A1 | 2/2009 | Hayter |
| 2009/0203982 A1 | 8/2009 | Nelson et al. |
| 2009/0240120 A1 | 9/2009 | Mensinger et al. |
| 2009/0284372 A1 | 11/2009 | Nelson et al. |
| 2009/0300616 A1 | 12/2009 | Sicurello et al. |
| 2010/0076280 A1 | 3/2010 | Bernstein et al. |
| 2010/0076288 A1 | 3/2010 | Connolly et al. |
| 2010/0076289 A1 | 3/2010 | Bernstein et al. |
| 2010/0076290 A1 | 3/2010 | Bernstein et al. |
| 2010/0076291 A1 | 3/2010 | Bernstein et al. |
| 2010/0076292 A1 | 3/2010 | Bernstein et al. |
| 2010/0076293 A1 | 3/2010 | Bernstein et al. |
| 2010/0082266 A1 | 4/2010 | Connolly et al. |
| 2010/0082364 A1 | 4/2010 | Taub et al. |
| 2010/0265073 A1 | 10/2010 | Harper |
| 2010/0275108 A1 | 10/2010 | Sloan et al. |
| 2010/0277342 A1 | 11/2010 | Sicurello et al. |
| 2010/0309001 A1 | 12/2010 | Connolly et al. |
| 2011/0015502 A1 | 1/2011 | Peyser |
| 2011/0015508 A1 | 1/2011 | Peyser |
| 2011/0015509 A1 | 1/2011 | Peyser |
| 2011/0044333 A1 | 2/2011 | Sicurello et al. |
| 2011/0046469 A1 | 2/2011 | Nelson et al. |
| 2011/0058485 A1 | 3/2011 | Sloan |
| 2011/0081888 A1 | 4/2011 | Waniss |
| 2011/0184265 A1 | 7/2011 | Hayter |
| 2011/0213225 A1 | 9/2011 | Bernstein et al. |
| 2011/0289497 A1 | 11/2011 | Kiaie et al. |
| 2012/0053428 A1 | 3/2012 | Bernstein et al. |
| 2012/0078071 A1 | 3/2012 | Bohm et al. |
| 2012/0092168 A1 | 4/2012 | Jennewine |
| 2012/0101352 A1 | 4/2012 | Peyser |
| 2012/0101353 A1 | 4/2012 | Reggiardo et al. |
| 2012/0158907 A1 | 6/2012 | Fennell et al. |
| 2012/0229299 A1* | 9/2012 | Skoldengen et al. .... 340/870.02 |
| 2012/0232368 A1* | 9/2012 | Jin et al. ........................ 600/365 |
| 2012/0245447 A1 | 9/2012 | Karan et al. |
| 2013/0035575 A1 | 2/2013 | Mayou et al. |
| 2013/0059541 A1 | 3/2013 | Sloan et al. |

FOREIGN PATENT DOCUMENTS

| | | |
|---|---|---|
| WO | WO 2006/079114 | 7/2006 |
| WO | WO 2008/106645 | 9/2008 |
| WO | WO 2009/018058 | 2/2009 |
| WO | WO 2009/105709 | 8/2009 |
| WO | WO 2009/146390 | 12/2009 |
| WO | WO 2009/146391 | 12/2009 |
| WO | WO 2010/039746 | 4/2010 |
| WO | WO 2012/010353 | 4/2012 |
| WO | WO 2012/108935 | 8/2012 |

OTHER PUBLICATIONS

Texas Instruments Incorporated: 1- and 8-Channel ANT RF Network Processors (2011).

* cited by examiner

| Alphanumeric | 5 Bit Value | Alphanumeric | 5 Bit Value | Alphanumeric | 5 Bit Value |
|---|---|---|---|---|---|
| 0 | 0x00 | A | 0x0A | M | 0x15 |
| 1 | 0x01 | B | 0x0B | N | 0x16 |
| 2 | 0x02 | C | 0x0C | P | 0x17 |
| 3 | 0x03 | D | 0x0D | Q | 0x18 |
| 4 | 0x04 | E | 0x0E | R | 0x19 |
| 5 | 0x05 | F | 0x0F | S | 0x1A |
| 6 | 0x06 | G | 0x10 | T | 0x1B |
| 7 | 0x07 | H | 0x11 | U | 0x1C |
| 8 | 0x08 | J | 0x12 | W | 0x1D |
| 9 | 0x09 | K | 0x13 | X | 0x1E |
|   |      | L | 0x14 | Y | 0x1F |

Note: Alphanumeric Values I, O, V and Z are Excluded $X_1 X_2 X_3 X_4 X_5 X_6 X_7$ $x_1x_1x_1x_1x_1 \; x_2x_2x_2x_2x_2 \; x_3x_3x_3x_3x_3 \; x_4x_4x_4x_4x_4 \; x_5x_5x_5x_5x_5 \; x_6x_6x_6x_6x_6 \; x_7x_7x_7x_7x_7$ 11bits — Device Number = Left Shift 11 bits +1

3bytes — Sensor Security Code = [00] [3 bytes]

SYSTEMS AND METHODS FOR PROCESSING AND TRANSMITTING SENSOR DATA

CROSS-REFERENCE TO RELATED APPLICATION

This application claims the benefit of U.S. Provisional Application No. 61/473,661 filed Apr. 8, 2011. The aforementioned application is incorporated by reference herein in its entirety, and is hereby expressly made a part of this specification.

FIELD

Systems and methods for processing, transmitting, and displaying data received from an analyte sensor, such as a glucose sensor, are provided.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In a first aspect, a method is provided of wirelessly exchanging glucose information between a first communication device associated with a continuous glucose sensor and a second communication device associated with a glucose information display device, the method comprising: transmitting a first beacon using the first communication device, the first beacon comprising a first device ID; receiving the first beacon using the second communication device; determining, using the second communication device, if the first device ID transmitted by the first communication device matches a second device ID stored at the second communication device; and executing an authentication protocol, using the second communication device, if the second communication device determines that the first device ID matches the second device ID.

In an embodiment of the first aspect, the method further comprises: receiving user input, using a user interface of the second communication device, comprising an identifier associated with the first communication device; and generating, using the second communication device, both the second device ID and a sensor security code.

In an embodiment of the first aspect, the identifier comprises a series of alphanumeric characters affixed to a housing of the first communication device and wherein the identifier is at least a portion of a manufacturer serial number associated with the first communication device.

In an embodiment of the first aspect, the first beacon further comprises a first challenge value and wherein executing the authentication protocol comprises generating, using the second communication device, a first authentication key based on the first challenge value and the sensor security code, wherein generating the authentication key comprises applying a hash algorithm using the first challenge value and the sensor security code.

In an embodiment of the first aspect, the method further comprises: transmitting, using the second communication device, a message having the authentication key and a request for glucose information; receiving, using the first communication device, the message; generating, using the first communication device, a second authentication key based on the first challenge value; determining, using the first communication device, if the first authentication key matches the second authentication key; and transmitting, using the first communication device, the requested glucose information if the first authentication key matches the second authentication key.

In an embodiment of the first aspect, generating the second authentication key is further based on a security code stored at the first communication device.

In an embodiment of the first aspect, the method further comprises establishing a communication channel between the first communication device and the second communication device if the first authentication key matches the second authentication key.

In an embodiment of the first aspect, the first communication device and the second communication device are configured to re-establish the communication channel at a predetermined time interval.

In an embodiment of the first aspect, the method further comprises closing the communication channel after a predetermined amount after transmitting the first beacon and transmitting, using the first communication device, a second beacon comprising the device ID and different challenge value after a predetermined amount of time since the transmission of the first beacon.

In an embodiment of the first aspect, the first communication device is a sensor system comprising a reusable sensor electronics module and the continuous glucose sensor, wherein the sensor electronics module comprises a processor and a transceiver, and wherein sensor system is configured to place the transceiver in a sleep mode after a predetermined amount of time since the transmission of the first beacon and place the transceiver in an operational mode after a predetermined amount of time since placing the transceiver in the sleep mode.

In a second aspect, a system is provided that wirelessly exchanges glucose information between a first communication device associated with a continuous glucose sensor and a second communication device associated with a glucose information display device, the system comprising: a sensor electronics module operatively coupled to a continuous glucose sensor, the sensor electronics module configured to wirelessly transmit a first beacon comprising a first device ID; and a display device comprising a display electronics module and a user interface, the user interface comprising an input module configured to receive user input and a display configured to display glucose information, wherein the display electronics module is configured to wirelessly receive the first beacon, determine if the first device ID transmitted by the first communication device matches a second device ID stored at the display device, and execute an authentication protocol if the second communication device determine that the first device ID matches the second device ID.

In an embodiment of the second aspect, the user interface of the display device is configured to accept user input representative of an identifier associated with the sensor electronics module and generate both the second device ID and a sensor security code.

In an embodiment of the second aspect, the identifier comprises a series of alphanumeric characters affixed to a housing of the sensor electronics module and wherein the identifier is at least a portion of a manufacturer serial number associated with the sensor electronics module.

In an embodiment of the second aspect, the first beacon further comprises a first challenge value and wherein executing the authentication protocol includes generating a first authentication key based on the first challenge value and the sensor security code, wherein generating the authentication key comprises applying a hash algorithm using the first challenge value and the sensor security code.

In an embodiment of the second aspect, the display device is further configured to transmit a message having the authentication key and a request for glucose information, and wherein the sensor electronics module is configured to receive the message, generate a second authentication key based on the first challenge value, determine if the first authentication key matches the second authentication key, and transmit the requested glucose information if the first authentication key matches the second authentication key.

In an embodiment of the second aspect, generating the second authentication key is further based on a security code stored at the sensor electronics module.

In an embodiment of the second aspect, the system is configured to establish a communication channel between the sensor electronics module and the display device if the first authentication key matches the second authentication key.

In an embodiment of the second aspect, the sensor electronics module and the display device are configured to re-establish the communication channel at a predetermined time interval.

In an embodiment of the second aspect, the system is further configured to close the communication channel after a predetermined amount since transmission of the first beacon, and wherein the sensor electronics module is configured to transmit a second beacon comprising the device ID and different challenge value after a predetermined amount of time since the transmission of the first beacon.

In an embodiment of the second aspect, the sensor electronics module is reusable with multiple continuous glucose sensors, wherein the sensor electronics module comprises a processor and a transceiver, and wherein sensor electronics module is configured to place the transceiver in a sleep mode after a predetermined amount of time since the transmission of the first beacon and place the transceiver in an operational mode after a predetermined amount of time since placing the transceiver in the sleep mode.

In a third aspect, a method is provided of managing real-time information in a system for monitoring a glucose concentration of a host, the system comprising a sensor electronics module operatively coupled to a continuous glucose sensor, and a display device, the method comprising: tracking time at a first, predetermined resolution at the sensor electronics module; generating, using the sensor electronics module, a glucose value; associating, using the sensor system, a time with the glucose value based on the time at the first resolution; tracking time at a second, predetermined resolution that is lower than the first resolution at the display device; translating, using the sensor electronics module, the time associated with the glucose value to the second resolution; and wirelessly transmitting, using the sensor system, the glucose value and the translated time to the display device.

In an embodiment of the third aspect, the first resolution is 125 milliseconds and the second resolution is 1 second.

In an embodiment of the third aspect, the method further comprises translating, using the sensor electronics module, time information received from the display device in the second resolution to the first resolution.

In an embodiment of the third aspect, the method further comprises receiving the translated time at the display device and determining, using the display device, if the translated time is in error by comparing the translated time to a threshold value.

In an embodiment of the third aspect, the method further comprises transmitting, using the display device, a request to time if the translated time is determined to be in error.

In a fourth aspect, a system is provided for monitoring a glucose concentration of a host that manages real-time information, the system comprising a sensor electronics module operatively coupled to a continuous glucose sensor, the sensor electronics module configured to track time at a first, predetermined resolution, generate a glucose value, associate a time with the glucose value based on the time at the first resolution, translate the time associated with the glucose value to a second resolution that is lower than the first resolution, and wirelessly transmit the glucose value and the translated time.

In an embodiment of the fourth aspect, the first resolution is 125 milliseconds and the second resolution is 1 second.

In an embodiment of the fourth aspect, the system further comprises a display device configured to receive the transmitted glucose value and the transmitted translated time, wherein the display device is configured to track time at the second resolution.

In an embodiment of the fourth aspect, the sensor electronics module is further configured to translate time information received from the display device in the second resolution to the first resolution.

In an embodiment of the fourth aspect, the display device is further configured to receive the translated time and determine if the translated time is in error by comparing the translated time to a threshold value.

In an embodiment of the fourth aspect, the display device is further configured to transmit a request to time if the translated time is determined to be in error.

In a fifth aspect, a method is provided of transmitting data between a first communication device associated with an analyte sensor and a second communication device associated with an analyte value display device, the method comprising: sending messages between the first communication device and the second communication device on a first schedule; requesting an analyte value calibration data point; sending messages between the first communication device and the second communication device on a second schedule more frequent than the first schedule; receiving the analyte value calibration point; calibrating analyte sensor data using the received analyte value calibration point; sending the calibrated analyte sensor data from the first communication device to the second communication device; and resuming sending messages between the first communication device and the second communication device on the first schedule.

In an embodiment of the fifth aspect, the resuming is responsive to the expiration of a predetermined amount of time.

In an embodiment of the fifth aspect, the resuming is responsive to the sending of the calibrated analyte sensor data.

In a sixth aspect, a system is provided for wirelessly transmitting data between a sensor electronics module operatively connected to a continuous glucose sensor and a display device, the system comprising computer-readable instructions stored in computer memory, wherein the instructions, when executed by one or more processors of the system, cause the system to: send messages between a sensor electronics module and a display device on a first schedule; send a request from the sensor electronics module to the display device for glucose reference data; send messages between the sensor electronics module and the display device on a second schedule more frequent than the first schedule; receive the glucose reference data; calibrate glucose sensor data generated by the continuous glucose sensor using the received glucose reference data; send the calibrated glucose sensor data from the sensor electronics module to the display device; and resume sending messages between the sensor electronics module and the display device on the first schedule.

In an embodiment of the sixth aspect, the resuming is responsive to the expiration of a predetermined amount of time.

In an embodiment of the sixth aspect, the resuming is responsive to the sending of the calibrated analyte sensor data.

In a seventh aspect, a method is provided for establishing a communication channel at a higher frequency between devices of a glucose monitoring system than a normal frequency of establishing the communication channel so that reference glucose measurement information can be more quickly exchanged, the method comprising: establishing a communication channel between a sensor electronics module operatively connected to a continuous glucose sensor and display device at a first frequency; determining that reference glucose measurement information is needed at the sensor electronics module; transmitting, using the sensor electronics module, a request to the display device for reference glucose measurement information during a first established communication channel; establishing the communication channel between a sensor electronics module and display device at a second frequency that is higher than the first frequency; prompting, using the display device, a user for reference glucose measurement information; transmitting, using the display device, the requested reference glucose measurement information; calculating, using the sensor electronics module, continuous glucose sensor data calibration information based on the reference glucose measurement information; and transmitting, using the sensor electronics module, the calibration information to the display device, wherein establishing the communication channel at the second frequency is maintained until a pre-determined condition is satisfied.

In an embodiment of the seventh aspect, the pre-determined condition is satisfied upon determining that the requested reference glucose measurement information is received by the sensor electronics module or the expiration of a predetermined amount of time.

In an embodiment of the seventh aspect, the sensor control module comprises a transceiver configured to transmit data to the display device, and wherein the method further comprises placing the transceiver in a low power mode in between the establishment of the communication channel.

In an embodiment of the seventh aspect, the establishment of the communication channel comprises transmitting a beacon using the sensor electronics module and receiving the beacon using the display device.

In an embodiment of the seventh aspect, the establishment of the communication channel further comprises initiating an authentication protocol.

In an eighth aspect, a system is provided for establishing a communication channel at a higher frequency between devices of a glucose monitoring system than a normal frequency of establishing the communication channel so that reference glucose measurement information can be more quickly exchanged, the system comprising computer-readable instructions stored in computer memory, wherein the instructions, when executed by one or more processors of the system, cause the system to: establish a communication channel between a sensor electronics module operatively connected to a continuous glucose sensor and display device at a first frequency; determine that reference glucose measurement information is needed at the sensor electronics module; transmit, using the sensor electronics module, a request to the display device for reference glucose measurement information during a first established communication channel; establish the communication channel between a sensor electronics module and display device at a second frequency that is higher than the first frequency; prompt, using the display device, a user for reference glucose measurement information; transmit, using the display device, the requested reference glucose measurement information; calculate, using the sensor electronics module, continuous glucose sensor data calibration information based on the reference glucose measurement information; and transmit, using the sensor electronics module, the calibration information to the display device, wherein establishing the communication channel at the second frequency is maintained until a pre-determined condition is satisfied.

In an embodiment of the eighth aspect, the pre-determined condition is satisfied upon determining that the requested reference glucose measurement information is received by the sensor electronics module or the expiration of a predetermined amount of time.

In an embodiment of the eighth aspect, the sensor control module comprises a transceiver configured to transmit data to the display device, and wherein the computer-readable instructions are configured to cause the system to place the transceiver in a low power mode in between the establishment of the communication channel.

In an embodiment of the eighth aspect, the establishment of the communication channel comprises transmitting a beacon using the sensor electronics module and receiving the beacon using the display device.

In an embodiment of the eighth aspect, the establishment of the communication channel further comprises initiating an authentication protocol.

In a ninth aspect, a method is provided of wirelessly exchanging glucose information between a first communication device associated with a continuous glucose sensor and a second communication device associated with a glucose information display device, the method comprising: transmitting a first beacon using the first communication device, the first beacon comprising a first device ID; receiving the first beacon using the second communication device; determining, using the second communication device, if the first device ID transmitted by the first communication device matches a second device ID stored at the second communication device; and executing an authentication protocol, using the second communication device, if the second communication device determines that the first device ID matches the second device ID.

In embodiment of the ninth aspect, or in connection with any other embodiment of the ninth aspect, the method further comprises receiving, using a user interface of the second communication device, user input comprising an identifier associated with the first communication device; and generating, using the second communication device, both the second device ID and a sensor security code.

In embodiment of the ninth aspect, or in connection with any other embodiment of the ninth aspect, the identifier comprises a series of alphanumeric characters affixed to a housing of the first communication device and wherein the identifier is at least a portion of a manufacturer serial number associated with the first communication device.

In embodiment of the ninth aspect, or in connection with any other embodiment of the ninth aspect, the first beacon further comprises a first challenge value and wherein executing the authentication protocol comprises generating, using the second communication device, a first authentication key based on the first challenge value and the sensor security code, wherein generating the authentication key comprises applying a hash algorithm using the first challenge value and the sensor security code.

In embodiment of the ninth aspect, or in connection with any other embodiment of the ninth aspect, the method comprises transmitting, using the second communication device, a message having the authentication key and a request for glucose information; receiving, using the first communication device, the message; generating, using the first communication device, a second authentication key based on the first challenge value; determining, using the first communication device, if the first authentication key matches the second authentication key; and transmitting, using the first communication device, the requested glucose information if the first authentication key matches the second authentication key.

In embodiment of the ninth aspect, or in connection with any other embodiment of the ninth aspect, generating the second authentication key is further based on a security code stored at the first communication device.

In embodiment of the ninth aspect, or in connection with any other embodiment of the ninth aspect, the method further comprises establishing a communication channel between the first communication device and the second communication device if the first authentication key matches the second authentication key.

In embodiment of the ninth aspect, or in connection with any other embodiment of the ninth aspect, the first communication device and the second communication device are configured to re-establish the communication channel at a predetermined time interval.

In embodiment of the ninth aspect, or in connection with any other embodiment of the ninth aspect, the method further comprises closing the communication channel after a predetermined amount after transmitting the first beacon and transmitting, using the first communication device, a second beacon comprising the device ID and different challenge value after a predetermined amount of time since the transmission of the first beacon.

In embodiment of the ninth aspect, or in connection with any other embodiment of the ninth aspect, the first communication device is a sensor system comprising a reusable sensor electronics module and the continuous glucose sensor, wherein the sensor electronics module comprises a processor and a transceiver, and wherein sensor system is configured to place the transceiver in a sleep mode after a predetermined amount of time since the transmission of the first beacon and place the transceiver in an operational mode uses more power than the sleep mode after a predetermined amount of time since placing the transceiver in the sleep mode.

In a tenth aspect, a continuous glucose monitoring system is provided, configured to perform the method of the ninth aspect or any of its embodiments.

In an eleventh aspect, a method is provided of managing real-time information in a system for monitoring a glucose concentration of a host, the system comprising a sensor electronics module operatively coupled to a continuous glucose sensor, and a display device, the method comprising: tracking time at a first, predetermined resolution at the sensor electronics module; generating, using the sensor electronics module, a glucose value; associating, using the sensor system, a time with the glucose value based on the time at the first resolution; tracking time at a second, predetermined resolution that is lower than the first resolution at the display device; translating, using the sensor electronics module, the time associated with the glucose value to the second resolution; and wirelessly transmitting, using the sensor system, the glucose value and the translated time to the display device.

In embodiment of the eleventh aspect, or in connection with any other embodiment of the eleventh aspect, the first resolution is 125 milliseconds and the second resolution is 1 second.

In embodiment of the eleventh aspect, or in connection with any other embodiment of the eleventh aspect, the method further comprises translating, using the sensor electronics module, time information received from the display device in the second resolution to the first resolution.

In embodiment of the eleventh aspect, or in connection with any other embodiment of the eleventh aspect, the method further comprises receiving the translated time at the display device and determining, using the display device, if the translated time is in error by comparing the translated time to a threshold value.

In embodiment of the eleventh aspect, or in connection with any other embodiment of the eleventh aspect, the method further comprises transmitting, using the display device, a request to reset time if the translated time is determined to be in error.

In a twelfth aspect, a continuous glucose monitoring system is provided configured, to perform the method of the eleventh aspect or any of its embodiments.

In a thirteenth aspect, a method is provided of transmitting data between a first communication device associated with an analyte sensor and a second communication device associated with an analyte value display device, the method comprising: sending messages between the first communication device and the second communication device on a first schedule; requesting an analyte value calibration data point; sending messages between the first communication device and the second communication device on a second schedule more frequent than the first schedule; receiving the analyte value calibration point; calibrating analyte sensor data using the received analyte value calibration point; sending the calibrated analyte sensor data from the first communication device to the second communication device; and resuming sending messages between the first communication device and the second communication device on the first schedule.

In embodiment of the thirteenth aspect, or in connection with any other embodiment of the thirteenth aspect, the resuming is responsive to the expiration of a predetermined amount of time.

In embodiment of the thirteenth aspect, or in connection with any other embodiment of the thirteenth aspect, the resuming is responsive to the sending of the calibrated analyte sensor data.

In a fourteenth aspect, a continuous glucose monitoring system is provided, configured to perform the method of the thirteenth aspect or any of its embodiments.

In a fifteenth aspect, a method is provided for establishing a communication channel at a higher frequency between devices of a glucose monitoring system than a normal frequency of establishing the communication channel so that reference glucose measurement information can be more quickly exchanged, the method comprising: establishing a communication channel between a sensor electronics module operatively connected to a continuous glucose sensor and a display device at a first frequency; determining that reference glucose measurement information is needed at the sensor electronics module; transmitting, using the sensor electronics module, a request to the display device for reference glucose measurement information during a first established communication channel; establishing the communication channel between a sensor electronics module and display device at a second frequency that is higher than the first frequency; prompting, using the display device, a user for reference glucose measurement information; transmitting, using the display device, the requested reference glucose measurement information; calculating, using the sensor electronics module, continuous glucose sensor data calibration information based on the reference glucose measurement information; and transmitting, using the sensor electronics module, the calibration information to the display device, wherein establishing the communication channel at the second frequency is maintained until a pre-determined condition is satisfied.

In embodiment of the fifteenth aspect, or in connection with any other embodiment of the fifteenth aspect, the pre-determined condition is satisfied upon determining that the requested reference glucose measurement information is received by the sensor electronics module or the expiration of a predetermined amount of time.

In embodiment of the fifteenth aspect, or in connection with any other embodiment of the fifteenth aspect, the sensor control module comprises a transceiver configured to transmit data to the display device, and wherein the method further comprises placing the transceiver in a low power mode in between the establishment of the communication channel.

In embodiment of the fifteenth aspect, or in connection with any other embodiment of the fifteenth aspect, the establishment of the communication channel comprises transmitting a beacon using the sensor electronics module and receiving the beacon using the display device.

In embodiment of the fifteenth aspect, or in connection with any other embodiment of the fifteenth aspect, the establishment of the communication channel further comprises initiating an authentication protocol.

In a sixteenth aspect, a continuous glucose monitoring system is provided, configured to perform the method of the fifteenth aspect or any of its embodiments.

DETAILED DESCRIPTION

Figure 1:
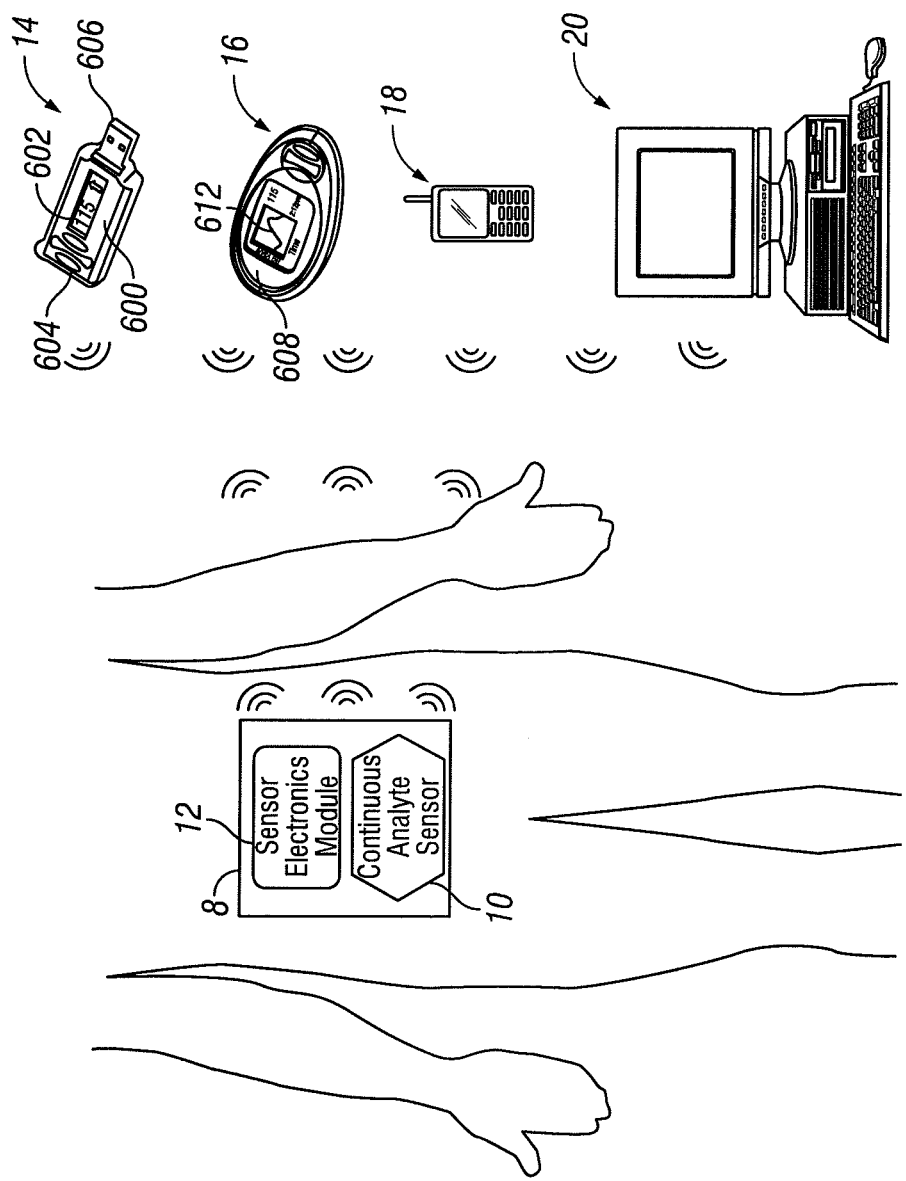
FIG. 1 is a diagram illustrating one embodiment of a continuous analyte sensor system including a sensor electronics module.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase;

conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, Plasmodium falciparum, poliovirus, Pseudomonas aeruginosa, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "A/D Converter" as used herein is a broad term and is to be given its ordinary and customary meaning to a person of ordinary skill in the art (and is not to be limited to a special or customized meaning), and furthermore refers without limitation to hardware and/or software that converts analog electrical signals into corresponding digital signals.

The terms "processor module," "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The terms "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "calibration" as used herein is a broad term and is to be given its ordinary and customary meaning to a person of ordinary skill in the art (and is not to be limited to a special or customized meaning), and furthermore refers without limitation to a process of determining a relationship between a raw data stream and corresponding reference data, which can be used to convert raw data into calibrated data (defined below). In some embodiments, such as continuous analyte sensors, for example, calibration can be updated or recalibrated over time as changes in the relationship between the raw data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average of the raw data stream.

The term "noise signal" as used herein is a broad term and is to be given its ordinary and customary meaning to a person of ordinary skill in the art (and is not to be limited to a special or customized meaning), and furthermore refers without limitation to a signal associated with noise on the data stream (e.g., non-analyte related signal). The noise signal can be determined by filtering and/or averaging, for example. In some embodiments, the noise signal is a signal residual, delta residual (difference of residual), absolute delta residual, and/or the like, which are described in more detail elsewhere herein.

The term "algorithm" as used herein is a broad term and is to be given its ordinary and customary meaning to a person of ordinary skill in the art (and is not to be limited to a special or customized meaning), and furthermore refers without limitation to a computational process (associated with computer programming or other written instructions) involved in transforming information from one state to another.

The term "matched data pairs" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein is a broad term and is to be given its ordinary and customary meaning to a person of ordinary skill in the art (and is not to be limited to a special or customized meaning), and furthermore refers without limitation to any device (or portion of a device) that measures a physical quantity and converts it into a signal that can be processed by analog and/or digital circuitry. Thus, the output of a sensor may be an analog and/or digital signal. Examples of sensors include analyte sensors, glucose sensors, temperature sensors, altitude sensors, accelerometers, and heart rate sensors.

The terms "glucose sensor" as used herein is a broad term and is to be given its ordinary and customary meaning to a person of ordinary skill in the art (and are not to be limited to a special or customized meaning), and furthermore refer without limitation to any sensor by which glucose can be quantified (e.g., enzymatic or non-enzymatic). For example, some embodiments of a glucose sensor may utilize a membrane that contains glucose oxidase that catalyzes the conversion of oxygen and glucose to hydrogen peroxide and gluconate, as illustrated by the following chemical reaction:

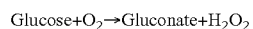

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "coupled", "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s), either directly or indirectly, in a manner that allows transmission of signals between the components. For example, modules of a computing device that communicate via a common data bus are coupled to one another. As another example, one or more electrodes of a glucose sensor can be used to detect the amount of glucose in a sample and convert that information into a signal, e.g., an electrical or electromagnetic signal; the signal can then be transmitted to an electronic circuit. In this case, the electrode is "operably linked" to the electronic circuitry, even though the analog signal from the electrode is transmitted and/or transformed by analog and/or digital circuitry before reaching the electronic circuit. These terms are broad enough to include wireless connectivity.

The term "physically connected" as used herein is a broad term and is to be given its ordinary and customary meaning to a person of ordinary skill in the art (and are not to be limited to a special or customized meaning), and furthermore refers without limitation to one or more components that are connected to another component(s) through direct contact and/or a wired connection, including connecting via one or more intermediate physically connecting component(s). For example, a glucose sensor may be physically connected to a sensor electronics module, and thus the processor module located therein, either directly or via one or more electrical connections.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammal, such as a human implanted with a device.

The term "continuous analyte sensor" as used herein is a broad term and is to be given its ordinary and customary meaning to a person of ordinary skill in the art (and is not to be limited to a special or customized meaning), and furthermore refers without limitation to a device, or portion of a device, that continuously or continually measures a concentration of an analyte, for example, at time intervals ranging from fractions of a second up to, for example, 1, 2, or 5 minutes, or longer. In one exemplary embodiment, a glucose sensor comprises a continuous analyte sensor, such as is described in U.S. Pat. No. 7,310,544, which is incorporated herein by reference in its entirety.

The term "continuous analyte sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer. In one embodiment, a glucose sensor performs continuous analyte sensing in order to monitor a glucose level in a corresponding host.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for a continuous analyte sensor, for example a self-monitoring blood glucose meter (SMBG) can be used as a reference for a continuous glucose sensor for comparison, calibration, and the like.

The term "clinical acceptability", as used herein, is a broad term and is to be given its ordinary and customary meaning to a person of ordinary skill in the art (and is not to be limited to a special or customized meaning), and refers without limitation to determination of the risk of inaccuracies to a patient. Clinical acceptability may consider a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. One example of clinical acceptability may be 85% of a given set of measured analyte values within the "A" and "B" region of a standard Clarke Error Grid when the sensor measurements are compared to a standard reference measurement.

The term "quality of calibration" as used herein, is a broad term and is to be given its ordinary and customary meaning to a person of ordinary skill in the art (and is not to be limited to a special or customized meaning), and refers without limitation to the statistical association of matched data pairs in the calibration set used to create the conversion function. For example, an R-value may be calculated for a calibration set to determine its statistical data association, wherein an R-value greater than 0.79 determines a statistically acceptable calibration quality, while an R-value less than 0.79 determines statistically unacceptable calibration quality.

The term "sensor session" as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of the sensor electronics module from the sensor housing).

The terms "noise," "noise event(s)," "noise episode(s)," "signal artifact(s)," "signal artifact event(s)," and "signal artifact episode(s)" as used herein are broad terms and are to be given their ordinary and customary meaning to a person of ordinary skill in the art (and are not to be limited to a special or customized meaning), and furthermore refer without limitation to signal noise that is substantially non-glucose related, such as interfering species, macro- or micro-motion, ischemia, pH changes, temperature changes, pressure, stress, or even unknown sources of mechanical, electrical and/or biochemical noise for example.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include sensor data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values. In some embodiments, estimated analyte values are estimated for a time period during which no data exists. However, estimated analyte values can also be estimated during a time period for which measured data exists, but is to be replaced by algorithmically extrapolated (e.g. processed or filtered) data due to noise or a time lag in the measured data, for example.

The term "calibration information" as used herein is a broad term and is to be given its ordinary and customary meaning to a person of ordinary skill in the art (and is not to be limited to a special or customized meaning), and furthermore refers without limitation to any information useful in calibration of a sensor. Calibration information may include reference data received from a reference analyte monitor, including one or more reference data points, one or more matched data pairs formed by matching reference data (e.g., one or more reference glucose data points) with substantially time corresponding sensor data (e.g., one or more continuous sensor data points), a calibration set formed from a set of one or more matched data pairs, a calibration line drawn from the calibration set, in vitro parameters (e.g., sensor sensitivity), and/or a manufacturing code, for example.

The term "alarm" as used herein is a broad term, and is to be given its ordinary and customary meaning to a person of ordinary skill in the art (and is not to be limited to a special or customized meaning), and furthermore refers without limitation to an alert or signal, such as an audible, visual, or tactile signal, triggered in response to one or more alarm conditions. In one embodiment, hyperglycemic and hypoglycemic alarms are triggered when present or predicted clinical danger is assessed based on continuous analyte data.

The term "transformed sensor data" as used herein is a broad term, and is to be given its ordinary and customary meaning to a person of ordinary skill in the art (and is not to be limited to a special or customized meaning), and furthermore refers without limitation to any data that is derived, either fully or in part, from raw sensor data from one or more sensors. For example, raw sensor data over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "sensor information" as used herein is a broad term, and is to be given its ordinary and customary meaning to a person of ordinary skill in the art (and is not to be limited to a special or customized meaning), and furthermore refers without limitation to information associated with measurement, signal processing (including calibration), alarms, data transmission, and/or display associated with a sensor, such as a continuous analyte sensor. The term is broad enough to include raw sensor data (one or more raw analyte concentration values), as well as transformed sensor data. In some embodiments, sensor information includes displayable sensor information.

The term "displayable sensor information" as used herein is a broad term, and is to be given its ordinary and customary meaning to a person of ordinary skill in the art (and is not to be limited to a special or customized meaning), and furthermore refers without limitation to information that is transmitted for display on one or more display devices. As is discussed elsewhere herein, the content of displayable sensor information that is transmitted to a particular display device may be customized for the particular display device. Additionally, formatting of displayable sensor information may be customized for respective display devices. Displayable sensor information may include any sensor data, including raw sensor data, transformed sensor data, and/or any information associated with measurement, signal processing (including calibration), and/or alerts associated with one or more sensors.

The term "data package" as used herein is a broad term, and is to be given its ordinary and customary meaning to a person of ordinary skill in the art (and is not to be limited to a special or customized meaning), and furthermore refers without limitation to a combination of data that is transmitted to one or more display devices, such as in response to triggering of an alert. A data package may include displayable sensor information (e.g., that has been selected and formatted for a particular display device) as well as header information, such as data indicating a delivery address, communication protocol, etc. Depending on the embodiment, a data package may comprises multiple packets of data that are separately transmitted to a display device (and reassembled at the display device) or a single block of data that is transmitted to the display device. Data packages may be formatted for transmission via any suitable communication protocol, including radio frequency, Bluetooth, universal serial bus, any of the wireless local area network (WLAN) communication standards, including the IEEE 802.11, 802.15, 802.20, 802.22 and other 802 communication protocols, and/or a proprietary communication protocol.

The term "direct wireless communication" as used herein is a broad term, and is to be given its ordinary and customary meaning to a person of ordinary skill in the art (and is not to be limited to a special or customized meaning), and furthermore refers without limitation to a data transmission that goes from one device to another device without any intermediate data processing (e.g., data manipulation). For example, direct wireless communication between a sensor electronics module and a display device occurs when the sensor information transmitted from the sensor electronics module is received by the display device without intermediate processing of the sensor information. The term is broad enough to include wireless communication that is transmitted through a router, a repeater, a telemetry receiver (e.g., configured to re-transmit the sensor information without additional algorithmic processing), and the like. The term is also broad enough to include transformation of data format (e.g., via a Bluetooth receiver) without substantive transformation of the sensor information itself.

The term "prospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in real-time (e.g., continuously and/or periodically as sensor data is received from the continuous analyte sensor) and provide real-time data output (e.g., continuously and/or periodically as sensor data is processed in the sensor electronics module).

The term "retrospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in retrospect, (e.g., analysis of a set of data for a time period previous to the present time period).

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

In some embodiments, a system is provided for continuous measurement of an analyte in a host that includes: a continuous analyte sensor configured to continuously measure a concentration of the analyte in the host and a sensor electronics module physically connected to the continuous analyte sensor during sensor use. In one embodiment, the sensor electronics module includes electronics configured to process a data stream associated with an analyte concentration measured by the continuous analyte sensor in order to generate displayable sensor information that includes raw sensor data, transformed sensor data, and/or any other sensor data, for example. The sensor electronics module may further be configured to generate displayable sensor information that is customized for respective display devices, such that different display devices may receive different displayable sensor information.

Alerts

In one embodiment, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In one embodiment, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In one embodiment, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. US-2007-0208246-A1, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data packaging indicating an alarm should be initiated by one or a plurality of display devices (e.g., sequentially and/or simultaneously). In some embodiments, the sensor electronics module determines which of the one or more alarms to trigger based on one or more alerts that are triggered. For example, when an alert triggers that indicates severe hypoglycemia, the sensor electronics module can perform multiple actions, such as activating an alarm on the sensor electronics module, transmitting a data package to a small (key fob) indicating activation of an alarm on the display, and transmitting a data package as a text message to a care provider. As an example, a text message can appear on a small (key fob) display, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one exemplary embodiment, the sensor electronics module is configured to search for and attempt to alarm a host or care provider sequentially using a list of display devices, such as: 1) a default display device, 2) a key fob device, 3) a cell phone (via auditory and/or visual methods, such as, text message to the host and/or care provider, voice message to the host and/or care provider, and/or 911).

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may comprise software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, PDAs, PCs and the like).

In some embodiments, certain display devices may be in direct wireless communication with the sensor electronics module, however intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In one embodiment, the sensor electronics module directly wirelessly transmits displayable sensor information to one or a plurality of display devices, such that the displayable sensor information transmitted from the sensor electronics module is received by the display device without intermediate processing of the displayable sensor information.

In one embodiment, one or more display devices comprise built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. However, any known authentication system or method useful for telemetry devices can be used with the preferred embodiments.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how they obtain sensor information.

In some embodiments, as described in more detail elsewhere herein, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Pat. No. 7,774,145, U.S. Patent Publication No. US-2007-0203966-A1, U.S. Patent Publication No. US-2007-0208245-A1, and U.S. Pat. No. 7,519,408, each of which are incorporated herein by reference in their entirety, describe systems and methods for providing an integral reference analyte monitor incorporated into a display device and/or other calibration methods that can be implemented with the preferred embodiments.

In general, a plurality of display devices (e.g., a small (key fob) display device, a larger (hand-held) display device, a mobile phone, a reference analyte monitor, a drug delivery device, a medical device and a personal computer) are configured to wirelessly communicate with the sensor electronics module, wherein the one or more display devices are configured to display at least some of the displayable sensor information wirelessly communicated from the sensor electronics module, wherein displayable sensor information includes sensor data, such as raw data and/or transformed sensor data, such as analyte concentration values, rate of change information, trend information, alert information, sensor diagnostic information and/or calibration information, for example.

Small (Key Fob) Display Device

In some embodiments, one the plurality of display devices is a small (e.g., key fob) display device 14 (FIG. 1) that is configured to display at least some of the sensor information, such as an analyte concentration value and a trend arrow. In general, a key fob device is a small hardware device with a built-in authentication mechanism sized to fit on a key chain. However, any small display device 14 can be configured with the functionality as described herein with reference to the key fob device 14, including a wrist band, a hang tag, a belt, a necklace, a pendent, a piece of jewelry, an adhesive patch, a pager, an identification (ID) card, and the like, all of which are included by the phrase "small display device" and/or "key fob device" herein.

In general, the key fob device 14 includes electronics configured to receive and display displayable sensor information (and optionally configured to query the sensor electronics module for the displayable sensor information). In one embodiment, the electronics include a RAM and a program storage memory configured at least to display the sensor data received from the sensor electronics module. In some embodiments, the key fob device 14 includes an alarm configured to warn a host of a triggered alert (e.g., audio, visual and/or vibratory). In some embodiments, the key fob device 14 includes a user interface, such as an LCD 602 and one or more buttons 604 that allows a user to view data, such as a numeric value and/or an arrow, to toggle through one or more screens, to select or define one or more user parameters, to respond to (e.g., silence, snooze, turn off) an alert, and/or the like.

In some embodiments, the key fob display device has a memory (e.g., such as in a gig stick or thumb drive) that stores sensor, drug (e.g., insulin) and other medical information, enabling a memory stick-type function that allows data transfer from the sensor electronics module to another device (e.g., a PC) and/or as a data back-up location for the sensor electronics module memory (e.g., data storage memory). In some embodiments, the key fob display device is configured to be automatically readable by a network system upon entry into a hospital or other medical complex.

In some embodiments, the key fob display device includes a physical connector, such as USB port 606, to enable connection to a port (e.g., USB) on a computer, enabling the key fob to function as a data download device (e.g., from the sensor electronics module to a PC), a telemetry connector (e.g., Bluetooth adapter/connector for a PC), and/or enables configurable settings on the key fob device (e.g., via software on the PC that allows configurable parameters such as numbers, arrows, trend, alarms, font, etc.) In some embodiments, user parameters associated with the small (key fob) display device can be programmed into (and/or modified) by a display device such as a personal computer, personal digital assistant, or the like. In one embodiment, user parameters include contact information, alert/alarms settings (e.g., thresholds, sounds, volume, and/or the like), calibration information, font size, display preferences, defaults (e.g., screens), and/or the like. Alternatively, the small (key fob) display device can be configured for direct programming of user parameters. In some embodiments, wherein the small (key fob) display device comprises a telemetry module, such as Bluetooth, and a USB connector (or the like), such that the small (key fob) display device additionally functions as telemetry adapter (e.g., Bluetooth adapter) enabling direct wireless communication between the sensor electronics module and the PC, for example, wherein the PC does not include the appropriate telemetry adapter therein.

Large (Hand-Held) Display Device

Figure 6:
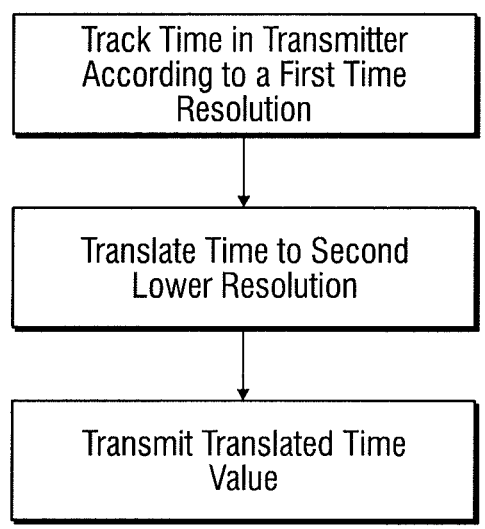
FIG. 6 is a flowchart illustrating one embodiment of an aspect of a process for translating high resolution time to lower resolution time.

In some embodiments, one the plurality of display devices is a hand-held display device 16 (FIG. 1) configured to display sensor information including an analyte concentration and a graphical representation of the analyte concentration over time. In general, the hand-held display device comprises a display 608 sufficiently large to display a graphical representation 612 of the sensor data over a time period, such as a previous 1, 3, 5, 6, 9, 12, 18, or 24-hours of sensor data. In some embodiments, the hand-held device 16 is configured to display a trend graph or other graphical representation, a numeric value, an arrow, and/or to alarm the host. U.S. Patent Publication No. US-2005-0203360-A1, which is incorporated herein by reference in its entirety, describes and illustrates some examples of display of data on a hand-held display device. Although FIG. 6 illustrates one embodiment of a hand-held display device, the hand-held device can be any single application device or multi-application device, such as mobile phone, a palm-top computer, a PDA, portable media player (e.g., iPod, MP3 player), a blood glucose meter, an insulin pump, and/or the like.

In some embodiments, a mobile phone (or PDA) is configured to display (as described above) and/or relay sensor information, such as via a voice or text message to the host and/or the host's care provider. In some embodiments, the mobile phone further comprises an alarm configured to warn a host of a triggered alert, such as in response to receiving a data package indicating triggering of the alert. Depending on the embodiment, the data package may include displayable sensor information, such as an on-screen message, text message, and/or pre-generated graphical representation of sensor data and/or transformed sensor data, as well as an indication of an alarm, such as an auditory alarm or a vibratory alarm, that should be activated by the mobile phone.

In some embodiments, one of the display devices is a drug delivery device, such as an insulin pump and/or insulin pen, configured to display sensor information. In some embodiments, the sensor electronics module is configured to wirelessly communicate sensor diagnostic information to the drug delivery device in order to enable to the drug delivery device to consider (include in its calculations/algorithms) a quality, reliability and/or accuracy of sensor information for closed loop and/or semi-closed loop systems, which are described in more detail in U.S. Pat. No. 7,591,801, which is incorporated herein by reference in its entirety. In some alternative embodiments, the sensor electronic module is configured to wirelessly communicate with a drug delivery device that does not include a display, for example, in order to enable a closed loop and/or semi-closed loop system as described above.

In some embodiments, one of the display devices is a drug delivery device is a reference analyte monitor, such as a blood glucose meter, configured to measure a reference analyte value associated with an analyte concentration in a biological sample from the host.

Personal Computer Display Device

In some embodiments, one of the display devices is personal computer (PC) 20 (FIG. 1) configured to display sensor information. Preferably, the PC 24 has software installed, wherein the software enables display and/or performs data analysis (retrospective processing) of the historic sensor information. In some embodiments, a hardware device can be provided (not shown), wherein the hardware device (e.g., dongle/adapter) is configured to plug into a port on the PC to enable wireless communication between the sensor electronics module and the PC. In some embodiments, the PC 24 is configured to set and/or modify configurable parameters of the sensor electronics module 12 and/or small (key fob device) 14, as described in more detail elsewhere herein.

Other Display Devices

In some embodiments, one of the display devices is an on-skin display device that is splittable from, releasably attached to, and/or dockable to the sensor housing (mounting unit, sensor pod, or the like). In some embodiments, release of the on-skin display turns the sensor off; in other embodiments, the sensor housing comprises sufficient sensor electronics to maintain sensor operation even when the on-skin display is released from the sensor housing.

In some embodiments, one of the display devices is a secondary device, such as a heart rate monitor, a pedometer, a temperature sensor, a car initialization device (e.g., configured to allow or disallow the car to start and/or drive in response to at least some of the sensor information wirelessly communicated from the sensor electronics module (e.g., glucose value above a predetermined threshold)). In some alternative embodiments, one of the display devices is designed for an alternative function device (e.g., a caller id device), wherein the system is configured to communicate with and/or translate displayable sensor information to a custom protocol of the alternative device such that displayable sensor information can be displayed on the alternative function device (display of caller id device).

Exemplary Configurations

FIG. 1 is a diagram illustrating one embodiment of a continuous analyte sensor system 8 including a sensor electronics module 12. In the embodiment of FIG. 1, the system includes a continuous analyte sensor 10 physically connected to a sensor electronics module 12, which is in direct wireless communication with a plurality of different display devices 14, 16, 18, and/or 20.

In one embodiment, the sensor electronics module 12 includes electronic circuitry associated with measuring and processing the continuous analyte sensor data, including prospective algorithms associated with processing and calibration of the sensor data. The sensor electronics module 12 may be physically connected to the continuous analyte sensor 10 and can be integral with (non-releasably attached to) or releasably attachable to the continuous analyte sensor 10. The sensor electronics module 12 may include hardware, firmware, and/or software that enables measurement of levels of the analyte via a glucose sensor, such as an analyte sensor. For example, the sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics module 12 includes sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544; 6,931,327; and 8,010,174, U.S. Patent Publication No. US-2007-0032706-A1, U.S. Patent Publication No. US-2007-0016381-A1, U.S. Patent Publication No. US-2008-0033254-A1, U.S. Patent Publication No. US-2005-0203360-A1, U.S. Pat. Nos. 7,519,408, 7,591,801, and 7,774,145, U.S. Patent Publication No. US-2007-0203966-A1 and U.S. Patent Publication No. US-2007-0208245-A1, each of which are incorporated herein by reference in their entirety.

Referring again to FIG. 1, a plurality of display devices (14, 16, 18, and/or 20) are configured for displaying (and/or alarming) the displayable sensor information that has been transmitted by the sensor electronics module 12 (e.g., in a customized data package that is transmitted to the display devices based on their respective preferences). For example, the display devices are configured to display the displayable sensor information as it is communicated from the sensor electronics module (e.g., in a data package that is transmitted to respective display devices), without any additional prospective processing required for calibration and real-time display of the sensor data.

In the embodiment of FIG. 1, the plurality of display devices includes a small (key fob) display device 14, such as a wrist watch, a belt, a necklace, a pendent, a piece of jewelry, an adhesive patch, a pager, a key fob, a plastic card (e.g., credit card), an identification (ID) card, and/or the like, wherein the small display device comprises a relatively small display (e.g., smaller than the large display device) and is configured to display certain types of displayable sensor information (e.g., a numerical value and an arrow, in some embodiments). In some embodiments, one of the plurality of display devices is a large (hand-held) display device 16, such as a hand-held receiver device, a palm-top computer and/or the like, wherein the large display device comprises a relatively larger display (e.g., larger than the small display device) and is configured to display a graphical representation of the continuous sensor data (e.g., including current and historic data). Other display devices can include other hand-held devices, such as a cell phone or PDA 18, an insulin delivery device, a blood glucose meter, and/or a desktop or laptop computer 24.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1, a plurality of different display devices are in direct wireless communication with the sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

Continuous Sensor

In some embodiments, a glucose sensor comprises a continuous sensor, for example a subcutaneous, transdermal (e.g., transcutaneous), or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

In one embodiment, the analyte sensor is an implantable glucose sensor, such as described with reference to U.S. Pat. No. 6,001,067 and U.S. Patent Publication No. US-2005-0027463-A1, each of which is hereby incorporated by reference in its entirety. In another embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, U.S. Patent Publication No. US-2008-0119703-A1, U.S. Patent Publication No. US-2008-0108942-A1, and U.S. Patent Publication No. US-2007-0197890-A1, each of which is hereby incorporated by reference in its entirety. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al., for example.

Figure 2A:
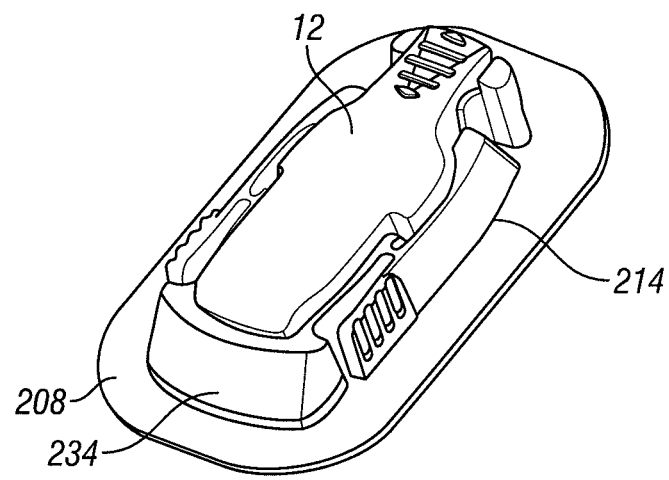
FIG. 2A is a perspective view of a sensor system including a mounting unit and sensor electronics module attached thereto according to one embodiment.
Figure 2B:
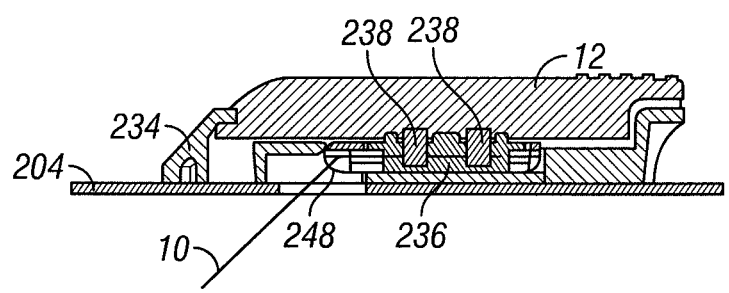
FIG. 2B is a side view of the sensor system of FIG. 2A.

FIGS. 2A and 2B are perspective and side views of a sensor system including a mounting unit 214 and sensor electronics module 12 attached thereto in one embodiment, shown in its functional position, including a mounting unit and a sensor electronics module matingly engaged therein. In some embodiments, the mounting unit 214, also referred to as a housing or sensor pod, comprises a base 234 adapted for fastening to a host's skin. The base can be formed from a variety of hard or soft materials, and can comprises a low profile for minimizing protrusion of the device from the host during use. In some embodiments, the base 234 is formed at least partially from a flexible material, which is believed to provide numerous advantages over conventional transcutaneous sensors, which, unfortunately, can suffer from motion-related artifacts associated with the host's movement when the host is using the device. The mounting unit 214 and/or sensor electronics module 12 can be located over the sensor insertion site to protect the site and/or provide a minimal footprint (utilization of surface area of the host's skin).

In some embodiments, a detachable connection between the mounting unit 214 and sensor electronics module 12 is provided, which enables improved manufacturability, namely, the relatively inexpensive mounting unit 214 can be disposed of when replacing the sensor system after its usable life, while the relatively more expensive sensor electronics module 12 can be reusable with multiple sensor systems. In some embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, contacts 238 are mounted on or in a subassembly hereinafter referred to as a contact subassembly 236 configured to fit within the base 234 of the mounting unit 214 and a hinge 248 that allows the contact subassembly 236 to pivot between a first position (for insertion) and a second position (for use) relative to the mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 238 are formed from a conductive elastomeric material, such as a carbon black elastomer, through which the sensor 10 extends.

In certain embodiments, the mounting unit 214 is provided with an adhesive pad 208, disposed on the mounting unit's back surface and includes a releasable backing layer. Thus, removing the backing layer and pressing the base portion 234 of the mounting unit onto the host's skin adheres the mounting unit 214 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety.

Use of Standardized Data Communication Protocols

Figure 3:
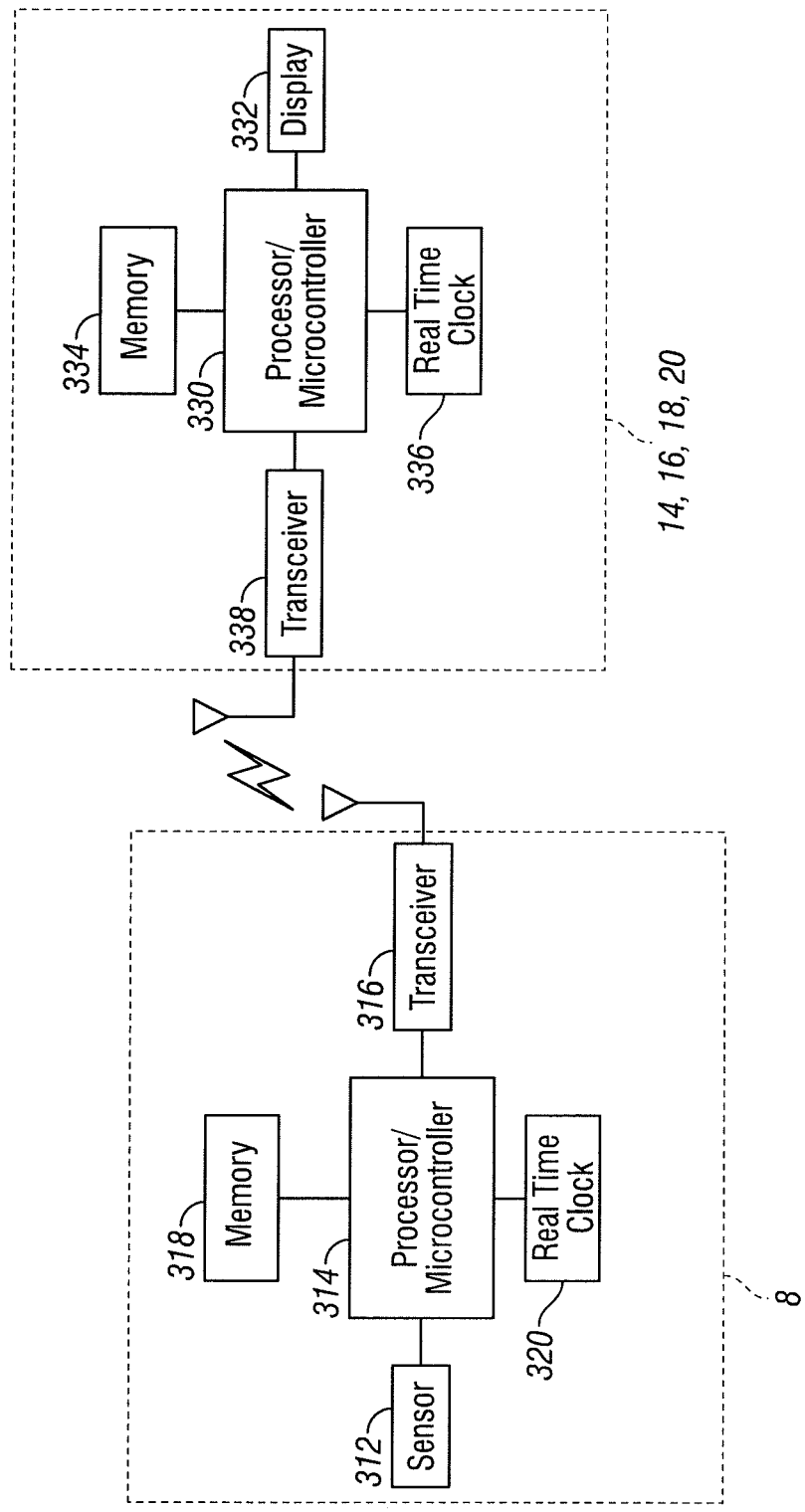
FIG. 3 is an exemplary block diagram illustrating various elements of one embodiment of a continuous analyte sensor system and display device.

FIG. 3 is an exemplary block diagram illustrating various elements of one embodiment of a continuous analyte sensor system 8 and display device 14, 16, 18, 20. The sensor system 8 may include a sensor 312 (also designated 10 in FIG. 1) coupled to a processor 314 (part of item 12 in FIG. 1) for processing and managing sensor data. The processor may be further coupled to a transceiver 316 (part of item 12 in FIG. 1) for sending sensor data and receiving requests and commands from an external device, such as the display device 14, 16, 18, 20, which is used to display or otherwise provide the sensor data to a user. The sensor system 8 may further include a memory 318 (part of item 12 in FIG. 1) and a real time clock 320 (part of item 12 in FIG. 1) for storing and tracking sensor data. Communication protocols and associated modulation schemes such as Bluetooth, Zigbee™, or ANT™ for example may be used to transmit and receive data between the sensor system 8 and the display device 14, 16, 18, 20.

The display device 14, 16, 18, 20 may be used for alerting and providing sensor information to a user, and may include a processor 330 for processing and managing sensor data. The display device 14, 16, 18, 20 may include a display 332, a memory 334, and a real time clock 336 for displaying, storing and tracking sensor data respectively. The display device 14, 16, 18, 20 may further include a transceiver 338 for receiving sensor data and for sending requests, instructions, and data to the sensor system 8. The transceiver 338 may further employ the communication protocols described above including, but not limited to, radio frequency, Bluetooth, BTLE, Zigbee™, ANT™, etc.

In some embodiments, when a standardized communication protocol is used such as Bluetooth or ANT, commercially available transceiver circuits may be utilized that incorporate processing circuitry to handle low level data communication functions such as the management of data encoding, transmission frequencies, handshake protocols, and the like. In these embodiments, the processor 314, 330 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver circuit.

The analyte sensor system 8 gathers analyte data that it periodically sends to the display device 14, 16, 18, 20. Rather than having the transmission and receiving circuitry continuously communicating, the analyte sensor system 8 and display device 14, 16, 18, 20 periodically establish a communication channel between them. Thus, sensor system 8 can communicate via wireless transmission (e.g., ANT+, low power Bluetooth, etc.) with display device 14, 16, 18, 20 (e.g., a hand-held computing device) at predetermined time intervals. The duration of the predetermined time interval can be selected to be long enough so that the sensor system 8 does not consume too much power by transmitting data more frequently than needed, yet frequent enough to provide substantially real-time sensor information (e.g., measured glucose values) to the display device 14, 16, 18, 20 for output (e.g., display) to a user. The predetermined time interval may be every five minutes, for example. It will be appreciated that this schedule can be varied to be any desired time interval between data transfer activity.

In between these data transfer procedures, the transceiver 316 of the analyte sensor system 8 can be powered down or in a sleep mode to conserve battery life. To establish a communication channel, the analyte sensor system 8 may send one or more message beacons every five minutes. Each message beacon may be considered an invitation for a display device 14, 16, 18, 20 to establish a communication channel with the sensor system 8. During initial system set up, the display device 14, 16, 18, 20 may listen continuously until such a message beacon is received. When the beacon is successfully received, the display device 14, 16, 18, 20 can acknowledge the reception to establish communication between the devices. When the desired data communication is complete, the channel can be broken, and the transceiver 316 of the analyte sensing system 8 (and possibly the transceiver 338 of the display device 14, 16, 18, 20 as well) can be powered down. After a five minute period, the transceivers 316, 338 can be powered up again substantially simultaneously, and establish a new communication channel using the same process to exchange any new data. This process may continue, with new communication channels being established at the pre-determined intervals. To allow for some loss of synchronization between the two devices in between transmissions, the analyte sensor system 8 may be configured to send a series of message beacons in a window of time around the scheduled transmission time (e.g., 8 message beacons per second for 4 seconds). Any one of the message beacons can be used to initiate the establishment of a new communication channel when it is received by the display device 14, 16, 18, 20.

Transceiver Pairing Scheme

In some communication protocols, pairing of two devices (a master and slave device) may be required to establish a relationship between two devices that want to communicate with one another. Pairing may be accomplished during the channel establishment process described above between the two devices. Establishing a channel may involve broadcasting a unique ID by one device and a search and acquisition of this ID by another device.

Within a conventional ANT protocol configuration, for example, a parameter that is typically used in device pairing is the master device ID. In order to establish an ANT channel, the master transmitter broadcasts its device ID (along with some other information) in the above described beacon and the receiver checks for the presence of the device ID of the transmitter with which it wants to communicate in received beacons. In a conventional ANT protocol, the device ID is a 2-byte value representing a specific master device.

Although the master device ID provides some level of security, in that a slave device can be programmed to communicate only with a master device having a particular device ID number, additional security can be useful in some embodiments. To provide additional security, some embodiments can use two pieces of information to pair a receiver with a particular transceiver device. These two pieces of information include the device ID described above and another value which is referred to herein as a sensor security code. The device ID is used as described above to filter receipt of non-matching messages at the lowest layer of the ANT radio protocol stack. The sensor security code is used for a key based authentication scheme at the software application layer of the system. In some embodiments, both the device ID and the sensor security code can be derived from an identifier (e.g., a manufacturer's serial number) associated with the sensor system 8 per the description below. As seen in the embodiment of FIG. 1, the sensor system 8 comprises two fundamental components, the continuous sensor 10 and the electronics module 12. These two components may be separable from one another, allowing, for example, replacement of the continuous sensor portion 10. In this case, the identifier may be etched into, printed on or otherwise attached to a housing of the electronics module portion 12.

The sensor system 8 may include a sensor system identifier, such as series of alphanumeric characters (e.g., a series of 5, 6, 7 or 8 alphanumeric characters) printed, etched or otherwise affixed on a housing of the sensor system 8, or any other known identifier, such as a bar code or quick response code. The sensor system identifier may be used to generate both the device ID used in the master beacons to establish a channel and to generate the sensor security code used for additional security in the glucose monitoring system. To maintain good data security, the alphanumeric characters and the sensor security code need not be transmitted over a wireless communication channel at any time.

Figures 4A, 4B:
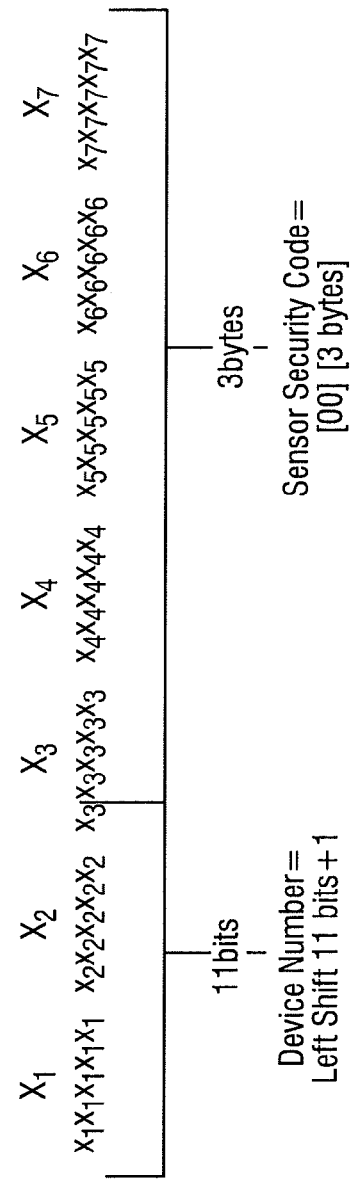
FIG. 4A provides an example of mapping an alphanumeric character to a five bit binary value.
FIG. 4B provides an example of mapping a 35 bit value to a device number and a transmitter ID.

In some embodiments where a series of seven alphanumeric characters are used as or associated with the sensor system identifier, the series alphanumeric characters are converted to seven 5 bit binary values as shown for example in FIG. 4A. These 35 bits are then concatenated together and divided into a device ID and sensor security code as shown for example in FIG. 4B. The most significant 11 bits, used for the device ID, are left-shifted by one bit and a one is inserted on the right, to produce a 12 bit value. Inserting the 1 on the right prevents the device number from being set to 0×0000. To produce a 16-bit device ID value, for example, four zeros can be used for the four most significant bits of the sequence. The remaining 24 bits of the original 35 concatenated bits can be used for the sensor security code.

As an example, a given seven character alphanumeric ID, 'A65S34F', is converted to binary as follows using the binary mappings shown in FIG. 4A,

A=01010
6=00110
5=00101
S=11010
3=00011
4=00100
F=01111

These binary values are concatenated to produce a 35 bit sequence:
01010001100010111010000110010001111

This 35 bit sequence is then separated to produce:
01010001100 and 01011101000011001000111

The device ID becomes 0000 0101 0001 1001 after a one is added as the least significant bit, and four zeros are added as the most significant bits. The other 24 bits are padded on the left with eight zeros to become the four byte value 0000 0000 0101 1101 0000 1100 1000 1111.

Therefore, the device ID becomes the two byte array [0x05][0x19] used as described above in the low level standardized communication protocol. The sensor security code becomes the four byte array [0x00][0x5D][0x0C][0x8F], used as described below.

When the analyte sensor system 8 is initially set up, the identifier associated with the system is entered into the display device 14, 16, 18, 20. Now, the sensor system 8 and the display device 14, 16, 18, 20 can each compute the same device ID and sensor security code using the algorithm described above.

Figure 5:
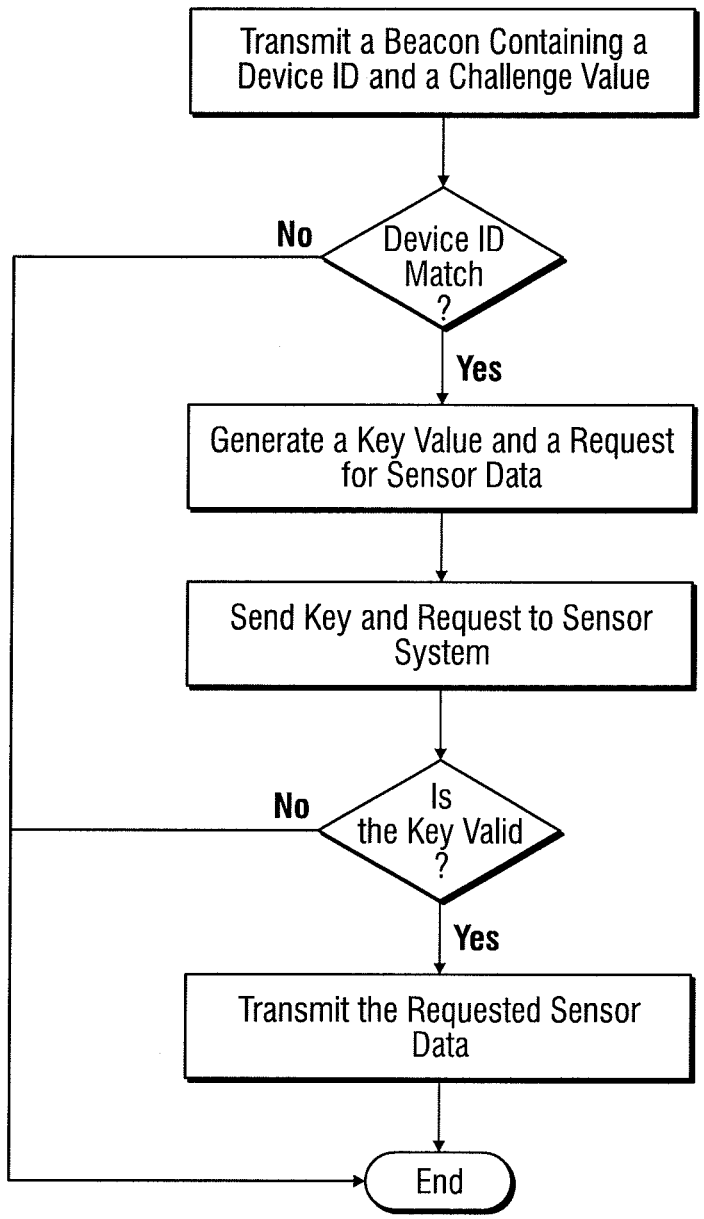
FIG. 5 is a flowchart illustrating one embodiment of an aspect of a process for pairing a transmitter with a receiver.

FIG. 5 is a flowchart illustrating one embodiment of an aspect of a process for pairing a transmitter with a receiver using a device ID and sensor security code. In block 501, the transceiver in the sensor system 8 sends one or more message beacons that include the device ID and a challenge value used in conjunction with the sensor security code as will be described below. In block 502, the display device 14, 16, 18, 20 may receive the transmission and determine whether to pair with the sensor system 8 by checking for a match between the device ID in the received beacon and the device ID it is searching for. If the device ID does not match, the pairing process can end, as shown in block 507. If the device ID does match, a communication channel is established. The part of the communication process involved in establishing a communication channel may be handled by the transceiver circuitry 316, 338 in accordance with the protocols established for the standardized communication and embedded in the transceiver circuitry. The processor 330 need not manage or even be aware of received beacons that do not contain the appropriate device ID.

If a communication channel is established, the challenge value is provided to the processor 330 to perform an additional authentication process as will now be described. The display device 14, 16, 18, 20 processes the challenge value using a predetermined algorithm and the sensor security code to produce a key value as shown in block 503, as well as generating a request for sensor data. In block 504, this key value is transmitted back to the sensor system 8 along with the request for information, such as sensor data stored in the sensor system 8. The request can be for a specific range of sensor data, such as the last hour's or day's worth of sensor data, or can be for the most current sensor data point. The sensor data can be glucose values in units of glucose concentration or can be raw data values in units of current or counts, for example. In block 505, the sensor system 8 receives and verifies the key sent by the display device 14, 16, 18, 20 using the same algorithm, challenge value and sensor security code. If the key is valid, the sensor system 8 transmits the requested sensor data to the display device 14, 16, 18, 20 as shown in block 506. Otherwise, as shown in block 507, the pairing process can end.

By using the method described with both the device ID and a sensor security code for communication authentication, two benefits are obtained. First, security is improved over using the device ID alone as authentication, because one weak link in device ID security is that the device ID is transmitted over the air in the message beacons. When the device ID is transmitted over the air, it could be intercepted by a hacker or other unauthorized user, and used to create a false receiver that could query the sensor system for user data. In addition, computational efficiency is improved because devices without matching device IDs need not authenticate with a receiver device using the challenge/response protocol before discovering that no communication between the devices should occur.

Time Handling Scheme within a Transmitter Device

Handling time in the sensor system 8 can be used for correct time stamping of generated and transmitted values as well as for processing data stored in the database of the sensor module in chronological order. Within some standardized communication protocols, such as ANT, absolute or real time is conventionally communicated at a resolution of whole seconds from a selected start time. However, the present inventors have found that higher resolution time tracking can be preferable in embodiments of glucose monitoring systems.

To allow for higher resolution time tracking, the sensor system 8 may connect a 32 kHz clock, for example, as input into a 32-bit counter, referred to as the real time clock (RTC) 320. By incrementing the counter every 4 k clock pulses, the counter will increment by one at 125 ms intervals. With this configuration, events occurring in the sensor system 8 can be tracked at a resolution of 125 msec, and the 32 bits of the counter allow for slightly more than seventeen years of tracked time before the counter will rollover. Time zero (e.g. the start of the 17 year period) can be selected that reasonably lasts the lifetime of the product.

Although the resolution and start time for the counter in the sensor system 8 described above may be advantageous for the sensor system 8, this time may now be incompatible with the time tracking of the communication system (e.g. conventional ANT). In situations where the time tracking is incompatible, the sensor system 8 may translate time coming into, and going out of, the transceiver 316.

FIG. 6 is a flowchart illustrating a process for translating high resolution time to lower resolution time in accordance with one embodiment. In block 601, a transmitter, such as a sensor system 8, may track time according to a first time resolution. The first time resolution may be a suitable resolution for use in sensor glucose data processing as described above. In block 602, the sensor system 8 translates time to a second resolution that is lower than the first resolution. The sensor system 8 may translate time both coming into, and going out of, the transceiver 316. For example, incoming time, based on seconds since the defined protocol start time, may be translated by subtracting the number of seconds between the sensor counter start time and the protocol start time to convert the incoming time into the number of seconds since the sensor counter start time. Outgoing time values may be translated by dividing the count by 8 to get whole seconds, and adding the number of seconds between the sensor counter start time and the protocol start time to convert the outgoing time into the number of seconds since the protocol start time. For outgoing time values, in block 603, the sensor system 8 transmits the translated time values.

The correct time, according to the number of seconds since the desired sensor system counter start time, may be set within the 32 bit counter at manufacturing. In some cases, errors may occur due to the different time resolutions being used to track time by the sensor system 8 and the display device 14, 16, 18, 20.

Figure 7:
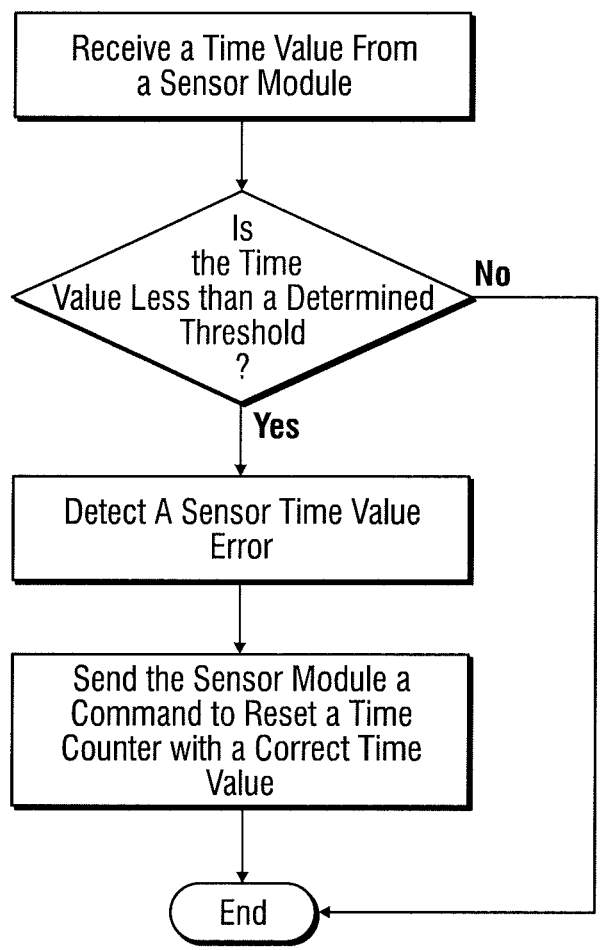
FIG. 7 is a flowchart illustrating one embodiment of a method for detecting an error in a time value received by a display device from a sensor electronics module.

FIG. 7 is a flowchart illustrating process for detecting an error in a time value received by a display device 14, 16, 18, 20 from a sensor system 8 in accordance with one embodiment. In block 701, a display device 14, 16, 18, 20 receives a time value from a sensor system 8. The sensor system 8 may have translated the time value as described above before sending the time value to the display device 14, 16, 18, 20. In block 702, the display device 14, 16, 18, 20 may determine whether the time value is less than a determined threshold. If the time value is not less than the determined threshold then the method may end at block 705. However, if the time value is less than a determined threshold, then the display device 14, 16, 18, 20 may determine that the sensor time value is an error, as shown in block 703. For example, during normal use, if the display device 14, 16, 18, 20 receives a time value from the transceiver 316 which is less than 0×10000000, then the display device 14, 16, 18, 20 may characterize this as an error condition. In block 704, the display device 14, 16, 18, 20 may send a command to the sensor system 8 to reset the time and provide the correct value for the number of seconds since the protocol start time, which the sensor system 8 may convert to 0.125 second counts since the sensor system start time. The corrected value may be written into the sensor system's 8 internal 32-bit counter RTC. The sensor system 8 may not overwrite the internal 32-bit counter RTC unless the 32-bit counter value is indeed smaller than 0×10000000.

By translating between time based on the protocol resolution and start time and time based on a higher resolution and different start time, the sensor system 8 maintains an internal count with a sub-second resolution of 125 ms which aids in debugging and overall system time granularity. At the same time, the sensor system 8 may be compatible with the external ANT ecosystem by communicating in terms of time based on the existing protocol convention. By keeping its own internal time set at manufacturing, the sensor system 8 can be assured to track time chronologically throughout the life of the system in non-error case scenarios. By allowing a display device 14, 16, 18, 20 to reset the time only when an inadvertent reset has been detected, (e.g. if the value is less than 0×10000000), the sensor system's 8 internal time can be corrected in case of a system error.

Interval Transmission Timing Protocol Accounting for Immediate Match Calibration In some embodiments, the sensor system 8 is responsible for calibrating continuous glucose sensor data. From time to time, the sensor system 8 may determine that a reference value (e.g., from a single point blood glucose meter) is needed to calibrate continuous glucose sensor data or otherwise update the sensor data based on the reference value. If a reference value is needed, the sensor system 8 may send a request to the display device 14, 16, 18, 20 to prompt the user for a reference value. The user may then obtain a reference value and input the reference value into the secondary display device 14, 16, 18, 20 by, for example, manually entering a reference value using input keys of the display device 14, 16, 18, 20.

It would be possible to incorporate this sample calibration interaction within the previously described five minute interaction periods. For example, the sensor system 8 could request a reference measurement in a first communication. Over the next few minutes, the user could obtain the measurement and enter it into the display device 14, 16, 18, 20. At the next communication period, the measurement could be sent to the sensor system 8 for calibration. At the next communication period five minutes later, updated and re-calibrated glucose measurements could be sent back to the display device 14, 16, 18, 20. Communicating at five minute intervals, for example, may help conserve power and increase the battery life of the sensor system 8.

However, this may not be optimal, since a fairly long period of time may pass before the user receives re-calibrated data. If there is a need to re-calibrate the data, the user may not have accurate glucose information. For example, in some embodiments the processing using the reference measurement is done by the sensor system 8, and this data is only periodically transmitted back to the display device 14, 16, 18, 20. This can delay receipt of calibrated data by the display device 14, 16, 18, 20. This is a situation that would be best to remedy as fast as possible.

Figure 8:
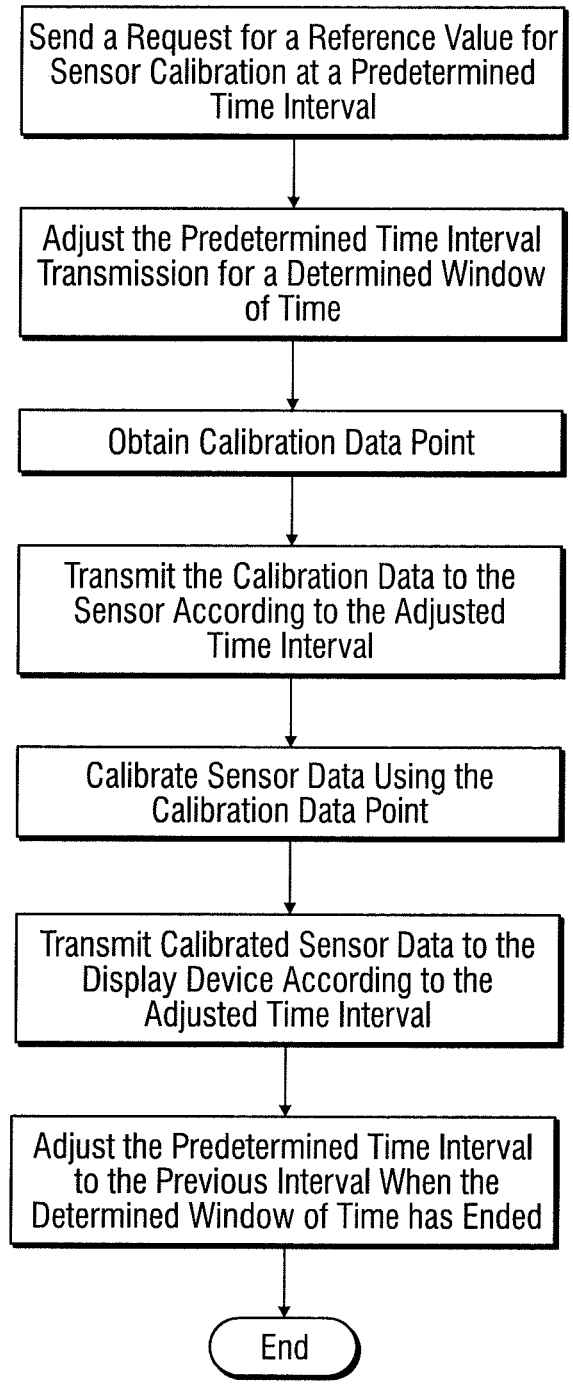
FIG. 8 is a flowchart illustrating one embodiment of a method for increasing the rate of reception of a display device for use when obtaining a reference value for sensor calibration.

FIG. 8 is a flowchart illustrating process for increasing the rate of reception of a display device for use when obtaining a reference value for sensor calibration in accordance with one embodiment. In block 801, the sensor system 8 sends a request for a reference value for sensor calibration at a predetermined time interval. The predetermined time interval may be five minutes, as described above. In block 802, to reduce the time required to update the user with re-calibrated data, the sensor system 8 and/or the display device 14, 16, 18, 20 may initiate adjustment of the predetermined time interval for a determined window of time to allow more frequent communication between the sensor system 8 and the display device 14, 16, 18, 20 as compared to the normal operation (i.e. at the predetermined time interval discussed above).

This window may be implemented by maintaining the established communication channel in operation after any request for a reference glucose measurement is made by the sensor system 8 instead of entering a power down state immediately after data transmission as is normally done when accurate data is being periodically transmitted. When the channel is open, the adjusted predetermined time interval for exchanging data may correspond to a relatively fast message rate, e.g. 0.5 Hz. In block 803, during the determined window of time, the user obtains and enters a measured glucose value to the display device 14, 16, 18, 20. In block 804, the display device 14, 16, 18, 20 transmits the calibration data to the sensor according to the adjusted time interval. By setting a short time interval (e.g., 0.5 Hz as described above), the measured glucose value data is essentially immediately transferred to the sensor system 8, which performs the necessary calibration. In block 805, the sensor system 8 may calibrate the sensor data using the calibration data point. In block 806, when the calibration is complete, newly calibrated data is essentially immediately transferred back to the display device 14, 16, 18, 20 using the existing adjusted time interval. In this way, at least one waiting period can be avoided.

The window of time during which the faster message rate (e.g., 0.5 Hz) is maintained may be selected to allow for enough time for a user to obtain and input the reference value into the secondary device. For example the window of time described above with reference to block 802 might be set for four minutes. In block 807, after the determined window of time closes, the sensor system 8 and the display device 14, 16,

18, 20 may adjust the predetermined time interval and return to communicating at the normal predetermined time interval.

In accordance with some embodiments, the sensor system 8 and display device 14, 16, 18, 20 are synchronized to re-establish a communication channel at a higher frequency so that reference measurement information can be more quickly exchanged. As an example, sensor system 8 and display device 14, 16, 18, 20 may be synchronized to normally establish a communication channel every five minutes, for example, where the communication channel closed prior to re-establishing the communication channel. However, when reference measurement information is needed, then the sensor system 8 and display device 14, 16, 18, 20 may be synchronized to establish a communication channel more frequently, such as every 30 seconds or every minute, instead of every five minutes. The more frequent establishment of a communication channel can be limited until one or more conditions are satisfied, after which the sensor system 8 and display device 14, 16, 18, 20 automatically revert back to the normal synchronization. The conditions can include the exchange of the requested reference information (e.g., the sensor system 8 receives the requested reference information from the display device), a predetermined amount of time (such as five or ten minutes) has expired since the establishment of the higher frequency synchronization, and the sensor system 8 transmitting calibration information based on the requested reference information to the display device.

The following is an exemplary process for exchanging reference information in which the frequency of establishing communication channels is increased accordance with one embodiment. First, the sensor system 8 and display device 14, 16, 18, 20 are synchronized to establish a communication channel at a first frequency, such as every five minutes. Next, the sensor system 8 determines that reference information (e.g., a reference measurement value) is needed. A reference measurement may be needed based upon a predetermined schedule of needing reference information (e.g., twice on the first day of using a new sensor, once on the second day of using the sensor, and once every other day thereafter), upon detection of an error (e.g., sensor system 8 determines a signal artifact in the sensor data or possible sensor malfunction based on an analysis of the sensor data) or a predetermined amount of time has expired since reference information was last received (e.g., last reference data was received 12 hours ago). The sensor system 8 then sends a request to the display device 14, 16, 18, 20 for the reference information during the next established communication channel. In response to the request, the sensor system 8 and display device 14, 16, 18, 20 adjust the synchronization frequency to a second frequency that is higher than the first frequency. In addition, in response to receiving the request for reference information, the display device 14, 16, 18, 20 may prompt a user via a user interface of the display device for reference information, and automatically transmit the requested reference information during the next established communication channel after the reference information is received. In this exemplary process, the second frequency is maintained until either the requested reference information is received by the sensor system 8 or the expiration of a predetermined amount of time, which ever occurs first. If the predetermined amount of time expires prior to receiving the requested reference information, the system reverts to the first synchronization frequency and the reference information is transmitted during the next established communication channel after the reference information is received by the display device 14, 16, 18, 20. The sensor system 8 can calculate calibration information based on the received reference information and send the calibration information to the display device using the communication channel that was established when the reference data was received or during a subsequent communication channel.

Note that one or more of the functions described in this document can be performed by software or firmware stored in memory (e.g. memory 318 and/or memory 334) and executed by one or more processors (e.g., processor 314 and/or processor 330). The firmware can also be stored and/or transported within any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any medium that can contain or store the program for use by or in connection with the instruction execution system, apparatus, or device. The computer readable medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

Methods and devices that may be suitable for use in conjunction with aspects of the preferred embodiments are disclosed in U.S. Pat. Nos. 4,994,167; 4,757,022; 6,001,067; 6,741,877; 6,702,857; 6,558,321; 6,931,327; 6,862,465; 7,074,307; 7,081,195; 7,108,778; 7,110,803; 7,192,450; 7,226,978; and 7,310,544.

Methods and devices that may be suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No.

US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No. US-2007-0016381-A1; U.S. Patent Publication No. US-2007-0027370-A1; U.S. Patent Publication No. US-2007-0027384-A1; U.S. Patent Publication No. US-2007-0032717-A1; U.S. Patent Publication No. US-2007-0032718-A1; U.S. Patent Publication No. US-2007-0059196-A1; U.S. Patent Publication No. US-2007-0066873-A1; U.S. Patent Publication No. US-2007-0093704-A1; U.S. Patent Publication No. US-2007-0197890-A1; U.S. Patent Publication No. US-2007-0173710-A1; U.S. Patent Publication No. US-2007-0163880-A1; U.S. Patent Publication No. US-2007-0203966-A1; U.S. Patent Publication No. US-2007-0213611-A1; U.S. Patent Publication No. US-2007-0232879-A1; U.S. Patent Publication No. US-2007-0235331-A1; U.S. Patent Publication No. US-2008-0021666-A1; and U.S. Patent Publication No. US-2008-0033254-A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/654,135 filed Jan. 17, 2007 and entitled "POROUS MEMBRANES FOR USE WITH IMPLANTABLE DEVICES"; U.S. patent application Ser. No. 11/654,140 filed Jan. 17, 2007 and entitled "MEMBRANES FOR AN ANALYTE SENSOR"; U.S. patent application Ser. No. 11/543,396 filed Oct. 4, 2006 and entitled "ANALYTE SENSOR"; U.S. patent application Ser. No. 11/543,490 filed Oct. 4, 2006 and entitled "ANALYTE SENSOR"; U.S. patent application Ser. No. 11/543,404 filed Oct. 4, 2006 and entitled "ANALYTE SENSOR"; U.S. patent application Ser. No. 11/691,426 filed Mar. 26, 2007 and entitled "ANALYTE SENSOR"; U.S. patent application Ser. No. 11/691,432 filed Mar. 26, 2007 and entitled "ANALYTE SENSOR"; U.S. patent application Ser. No. 11/691,424 filed Mar. 26, 2007 and entitled "ANALYTE SENSOR"; and U.S. patent application Ser. No. 11/691,466 filed Mar. 26, 2007 and entitled "ANALYTE SENSOR".

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for wirelessly exchanging glucose information between a first communication device associated with a continuous glucose sensor and a second communication device associated with a glucose information display device, the method comprising:
   receiving user input, using a user interface of the second communication device, comprising an identifier associated with the first communication device; and
   generating and storing, using the second communication device, a second device ID based at least partially on the identifier;
   transmitting a first beacon using the first communication device, the first beacon comprising a first device ID;
   receiving the first beacon using the second communication device;
   determining, using the second communication device, if the first device ID transmitted by the first communication device matches the second device ID stored at the second communication device;
   executing an authentication protocol based on the second communication device determining that the first device ID matches the second device ID; and
   exchanging glucose information between the first communication device and the second communication device upon successful completion of the authentication protocol,
   wherein the authentication protocol includes
      generating, using the second communication device, a first authentication key using a hash function applied to a challenge value provided by the first communication device and the identifier associated with the first communication device,
      transmitting, using the second communication device, a message having the first authentication key,
      receiving, using the first communication device, the message,
      generating, using the first communication device, a second authentication key based on the first challenge value, and
      determining, using the first communication device, if the first authentication key matches the second authentication key.

2. The method of claim 1, wherein the identifier comprises a series of alphanumeric characters affixed to a housing of the first communication device and wherein the identifier is at least a portion of a manufacturer serial number associated with the first communication device.

3. The method of claim 1, wherein generating the second authentication key is further based on a security code stored at the first communication device.

4. The method of claim 1, further comprising establishing a communication channel between the first communication device and the second communication device if the first authentication key matches the second authentication key.

5. The method of claim 4, wherein the first communication device and the second communication device are configured to re-establish the communication channel at a predetermined time interval.

6. The method of claim 4, further comprising closing the communication channel after a predetermined amount after transmitting the first beacon and transmitting, using the first communication device, a second beacon comprising the device ID and different challenge value after a predetermined amount of time since the transmission of the first beacon.

7. The method of claim 1, wherein the message transmitted using the second communication device further includes a request for glucose information, and wherein the first communication device transmits the requested glucose information if the first authentication key matches the second authentication key.

8. A method for wirelessly exchanging glucose information between a first communication device associated with a continuous glucose sensor and a second communication device associated with a glucose information display device, the method comprising:
    transmitting a first beacon using the first communication device, the first beacon comprising a first device ID:
    receiving the first beacon using the second communication device;
    determining, using the second communication device, if the first device ID transmitted by the first communication device matches the second device ID stored at the second communication device;
    executing an authentication protocol between the first communication device and the second communication device if the first device ID matches the second device ID, wherein the authentication protocol includes generating, using the second communication device, a first authentication key using a hash function applied to a challenge value provided by the first communication device and an identifier associated with the first communication device; and
    exchanging glucose information between the first communication device and the second communication device upon successful completion of the authentication protocol,
    wherein the first communication device is a sensor system comprising a reusable sensor electronics module and the continuous glucose sensor, wherein the sensor electronics module comprises a processor and a transceiver, and wherein sensor system places the transceiver in a sleep mode after a predetermined amount of time since opening a transmission window and places the transceiver in an operational mode after a predetermined amount of time since placing the transceiver in the sleep mode.

9. A system for wirelessly exchanging glucose information between a first communication device associated with a continuous glucose sensor and a second communication device associated with a glucose information display device, the system comprising:
    a sensor electronics module operatively coupled to a continuous glucose sensor, the sensor electronics module configured to wirelessly transmit a first beacon comprising a first device ID; and
    a display device comprising a display electronics module and a user interface, the user interface comprising an input module configured to receive user input and the display device configured to display glucose information,
    wherein the user interface of the display device is configured to accept user input representative of an identifier associated with the sensor electronics module,
    wherein the display electronics module is configured to generate and store a second device ID at least partially based on the identifier, wirelessly receive the first beacon, and determine if the first device ID transmitted by the first communication device matches the second device ID stored at the display device,
    wherein the system executes an authentication protocol based on the display device determining that the first device ID matches the second device ID, the authentication protocol including
        the display device generating a first authentication key based on a challenge value provided by the sensor electronics module and a sensor electronics ID inputted by a user into the display device, wherein generating the authentication key comprises applying a hash algorithm using the challenge value and the sensor electronics ID, transmitting a message having the first authentication key, and
        the sensor electronics receiving the message, generating a second authentication key based on the challenge value and a sensor electronics ID stored in the sensor electronics module during manufacturing, and determining if the first authentication key matches the second authentication key, and
    wherein the sensor electronics module and the display device exchange data configured to exchange glucose information upon successful completion of the authentication protocol.

10. The system of claim 9, wherein the sensor electronics ID inputted by the user comprises a series of alphanumeric characters affixed to a housing of the sensor electronics module.

11. The system of claim 9, wherein generating the second authentication key is further based on a security code stored at the sensor electronics module.

12. The system of claim 9, wherein the system is configured to establish a communication channel between the sensor electronics module and the display device if the first authentication key matches the second authentication key.

13. The system of claim 12, wherein the sensor electronics module and the display device are configured to re-establish the communication channel at a predetermined time interval.

14. The system of claim 12, wherein the system is further configured to close the communication channel after a predetermined amount since transmission of the first beacon, and wherein the sensor electronics module is configured to transmit a second beacon comprising the device ID and different challenge value after a predetermined amount of time since the transmission of the first beacon.

15. A system for wirelessly exchanging glucose information between devices of a continuous glucose monitoring system, the system comprising:
    a sensor electronics module operatively coupled to a continuous glucose sensor, the sensor electronics module configured to generate, process and transmit glucose data indicative of a host's glucose concentration measured by the glucose sensor; and
    a display device configured to wirelessly communicate with the sensor electronics module, the display device comprising a display electronics module and a user interface, the user interface comprising an input module configured to receive user input and a display configured to display glucose information, wherein the sensor electronics module is configured to wirelessly transmit a first beacon comprising a first device ID, wherein the display electronics module is configured to wirelessly receive the first beacon, determine if the first device ID transmitted by the first communication device matches a second device ID stored at the display device, and execute an authentication protocol if the second communication device determines that the first device ID matches the second device ID, wherein the authentication protocol includes the display device generating a first authentication key based on a challenge value provided by the sensor electronics module and a sensor electronics ID inputted by a user into the display device, and applying a hash algorithm using the challenge value and the sensor electronics ID, and wherein the sensor electronics module is reusable with multiple continuous glucose sensors, wherein the sensor electronics module comprises a processor and a transceiver, and wherein sensor electronics module is configured to place the transceiver in a sleep mode after a predetermined amount of time since opening a transmission window and place the transceiver in an operational mode after a predetermined amount of time since placing the transceiver in the sleep mode.

* * * * *

UNITED STATES PATENT AND TRADEMARK OFFICE
CERTIFICATE OF CORRECTION

PATENT NO. : 8,844,007 B2  
APPLICATION NO. : 13/441621  
DATED : September 23, 2014  
INVENTOR(S) : Ken San Vicente et al.

Page 1 of 1

It is certified that error appears in the above-identified patent and that said Letters Patent is hereby corrected as shown below:

On the Title Page

In column 2 (page 1, item 56) at line 12, Under Other Publications, before "2007" delete "1".

In the Specification

In column 10 at lines 63-64, Change "andrenostenedione;" to --androstenedione;--.

In column 11 at line 12, Change "diptheria" to --diphtheria--.

In column 11 at line 16, Change "tri-iodothyronine" to --triiodothyronine--.

In column 11 at line 19, Change "perioxidase;" to --peroxidase;--.

In column 11 at line 27, Change "tri-iodothyronine" to --triiodothyronine--.

In column 11 at line 28, Change "sissomicin;" to --sisomicin;--.

In column 11 at line 32, Change "duodenalisa," to --duodenalis,--.

In column 11 at line 40, Change "Trepenoma pallidium," to --Treponema pallidum,--.

In column 11 at line 41, Change "stomatis" to --stomatitis--.

In column 11 at line 61, Change "(barbituates," to --(barbiturates,--.

In column 27 at line 46, Change "matingly" to --mattingly--.

In the Claims

In column 41 at line 30, In Claim 8, Change "ID:" to --ID;--.

In column 42 at line 18, In Claim 9, change "including" to --including,--.

Signed and Sealed this  
Fourteenth Day of April, 2015

Michelle K. Lee  
*Director of the United States Patent and Trademark Office*